(12) United States Patent
Kuyler

(10) Patent No.: US 12,156,820 B2
(45) Date of Patent: Dec. 3, 2024

(54) SPINAL IMPLANT SYSTEM AND METHOD

(71) Applicant: WARSAW ORTHOPEDIC INC., Warsaw, IN (US)

(72) Inventor: Adriaan J. Kuyler, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 299 days.

(21) Appl. No.: 17/494,935

(22) Filed: Oct. 6, 2021

(65) Prior Publication Data
US 2022/0023070 A1     Jan. 27, 2022

Related U.S. Application Data

(62) Division of application No. 16/395,928, filed on Apr. 26, 2019, now Pat. No. 11,160,670.

(51) Int. Cl.
*A61F 2/46*     (2006.01)

(52) U.S. Cl.
CPC .......... *A61F 2/4611* (2013.01); *A61F 2/4601* (2013.01); *A61F 2/4603* (2013.01); *A61F 2002/4627* (2013.01)

(58) Field of Classification Search
CPC .. A61F 2/4601; A61F 2/4611; A61F 2/30771; A61F 2002/4623; A61F 2002/4627
See application file for complete search history.

(56) References Cited

U.S. PATENT DOCUMENTS

| | | | |
|---|---|---|---|
| 5,766,252 A | 6/1998 | Henry et al. | |
| 5,989,289 A | 11/1999 | Coates et al. | |
| 6,174,311 B1 | 1/2001 | Branch et al. | |
| 6,530,955 B2 | 3/2003 | Boyle et al. | |
| 7,575,580 B2 | 8/2009 | Lim et al. | |
| 9,039,774 B2 | 5/2015 | Chataigner et al. | |
| 9,095,385 B2 | 8/2015 | Wallenstein et al. | |
| 10,004,609 B2 | 6/2018 | Palmatier et al. | |
| 10,022,245 B2 | 7/2018 | Frasier et al. | |
| 2005/0203538 A1 | 9/2005 | Lo et al. | |
| 2006/0111767 A1* | 5/2006 | Olson ..................... | A61N 1/05 607/116 |

(Continued)

OTHER PUBLICATIONS

European Patent Office, 80298 Munich, Germany, Extended European Search Report, Application No. 19925887.2—PCT/US2019057116, Date Nov. 25, 2022.

*Primary Examiner* — Anu Ramana
(74) *Attorney, Agent, or Firm* — Sorell, Lenna & Schmidt, LLP

(57) ABSTRACT

An instrument includes a sleeve extending between proximal and distal ends. The sleeve defines a passageway. The distal end defines an engagement portion including an engagement surface extending from a first end to a second end. A peg extends outwardly from the first end. An opening that is in communication with the passageway extends through the second end. A knob is coupled to the proximal end. A shaft includes a proximal end and an opposite distal end. The distal end of the shaft includes a mating portion. The mating portion extends through the opening. The proximal end of the shaft is coupled to the knob. The knob is rotatable relative to the sleeve to rotate the shaft relative to the sleeve. Methods of use are disclosed.

18 Claims, 23 Drawing Sheets

(56) References Cited

U.S. PATENT DOCUMENTS

| | | |
|---|---|---|
| 2006/0235426 A1 | 10/2006 | Lim et al. |
| 2007/0093850 A1 | 4/2007 | Harris et al. |
| 2007/0093897 A1 | 4/2007 | Gerbec et al. |
| 2007/0142843 A1 | 6/2007 | Dye |
| 2007/0162128 A1 | 7/2007 | Deridder et al. |
| 2007/0213737 A1 | 9/2007 | Schermerhorn et al. |
| 2007/0225726 A1 | 9/2007 | Dye et al. |
| 2008/0027544 A1 | 1/2008 | Melkent |
| 2008/0097454 A1 | 4/2008 | Deridder et al. |
| 2009/0265008 A1 | 10/2009 | Thibodeau |
| 2011/0301710 A1 | 12/2011 | Mather |
| 2012/0130387 A1 | 5/2012 | Simpson et al. |
| 2012/0296428 A1* | 11/2012 | Donner .............. A61B 17/7043 623/17.11 |
| 2013/0282018 A1 | 10/2013 | Deridder et al. |
| 2014/0142642 A1 | 5/2014 | Wallenstein et al. |
| 2014/0277493 A1 | 9/2014 | Glad et al. |
| 2015/0265420 A1 | 9/2015 | Lynn et al. |
| 2016/0128847 A1 | 5/2016 | Kurtaliaj et al. |

\* cited by examiner

| Lattice Calculator | |
|---|---|
| Dimension | Value |
| X dimension (mm) | 1 |
| Y dimension (mm) | 1.75 |
| Z dimension (mm) | 2.75 |
| xy plane diagonal (mm) | 2.02 |
| half diagonal = base | 1.01 |
| half Z = height (mm) | 1.38 |
| Resulting unit cell Z angle | 0.94 |
| Build Angle Relative to unit Z axis (degrees) | 53.8 0 |
| Build Angle (degrees) | 53.8 |

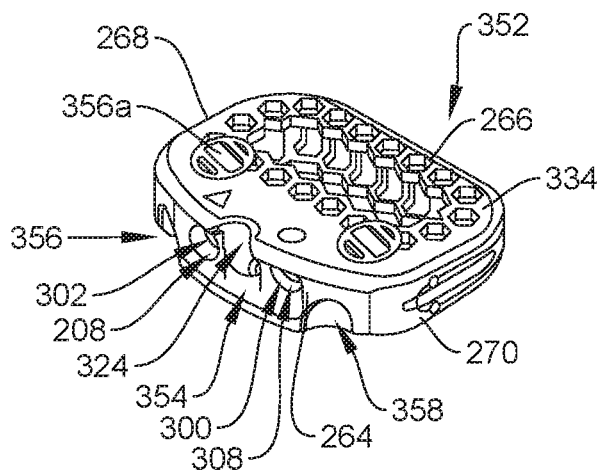
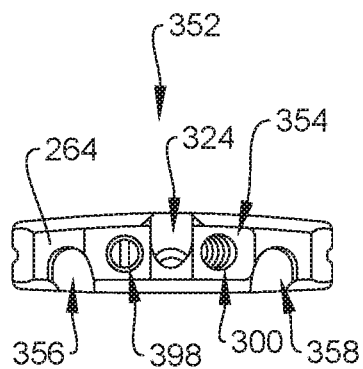
FIG. 42  FIG. 43
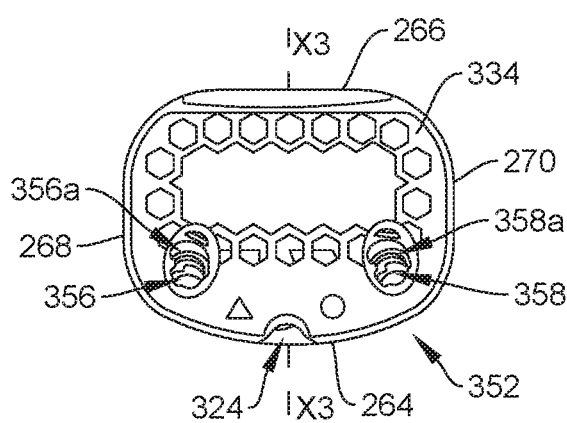
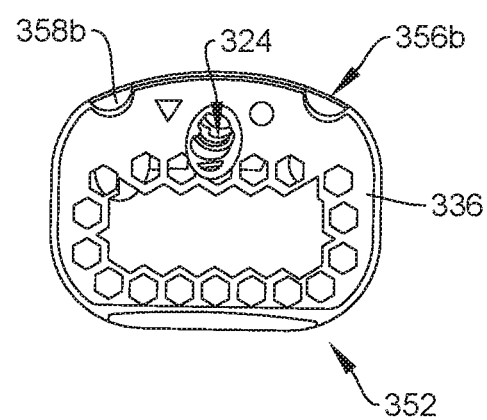
FIG. 44  FIG. 45
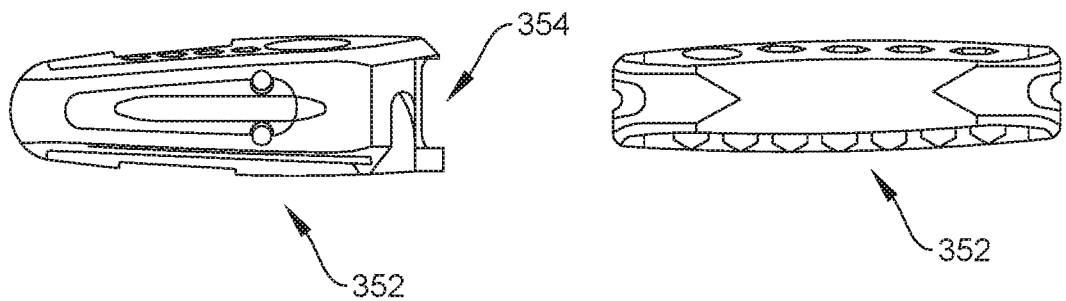
FIG. 46  FIG. 47

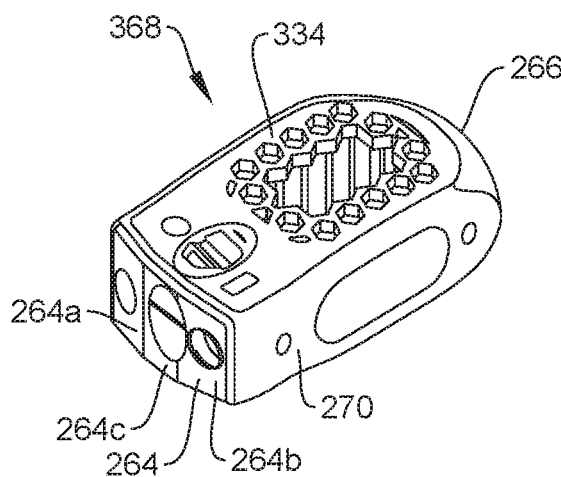
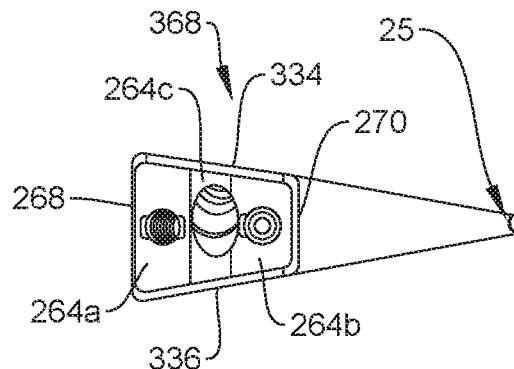
FIG. 66  FIG. 67
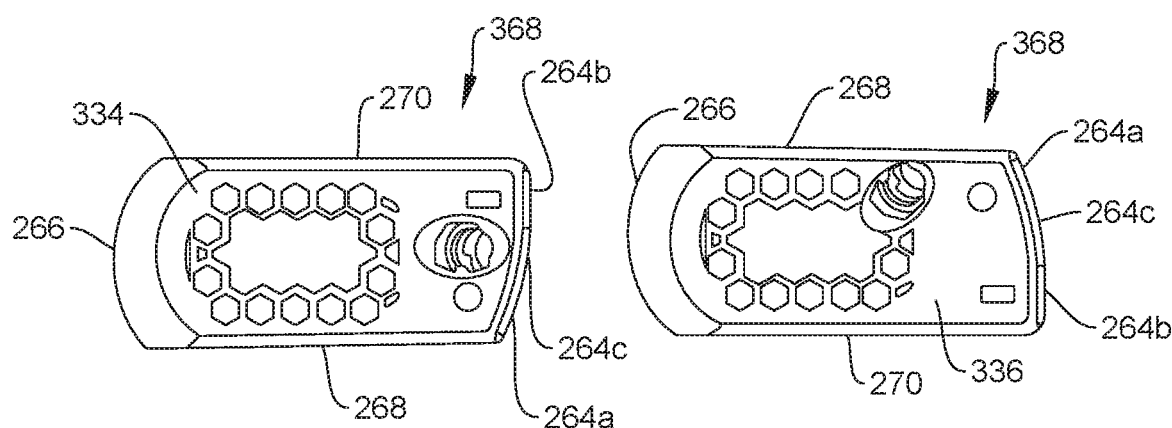
FIG. 68  FIG. 69
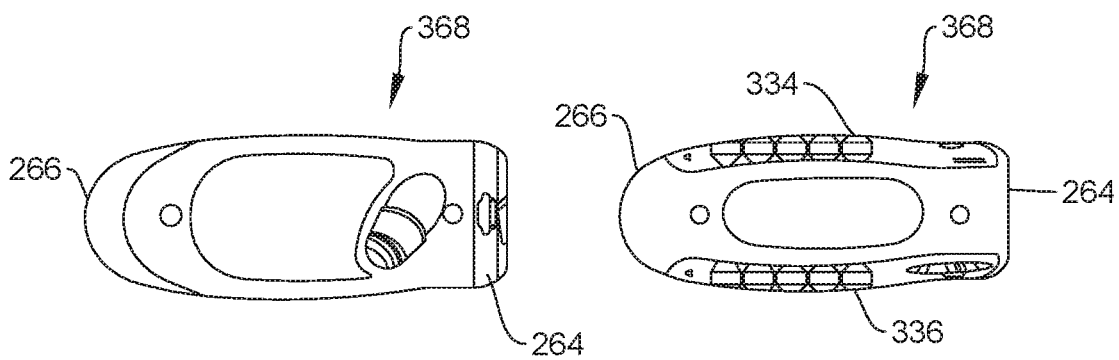
FIG. 70  FIG. 71

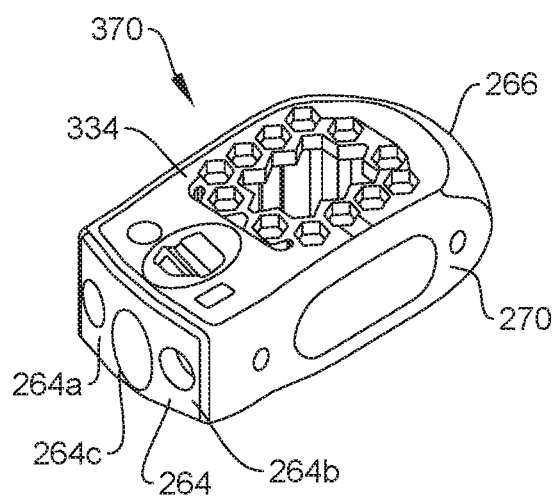
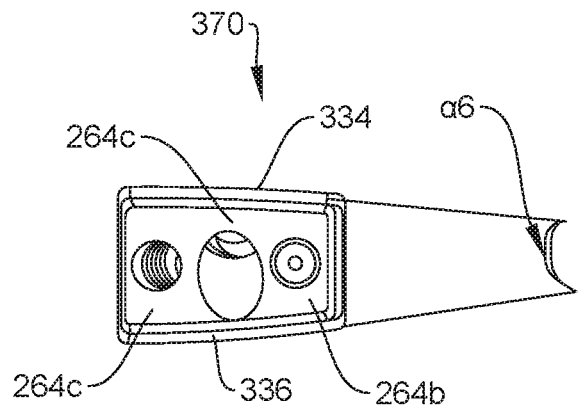
FIG. 72
FIG. 73
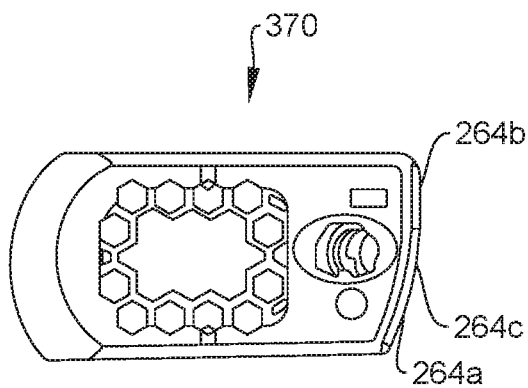
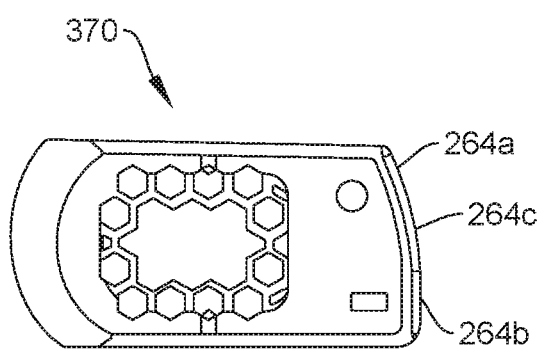
FIG. 74
FIG. 75
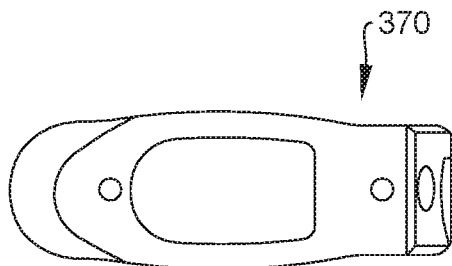
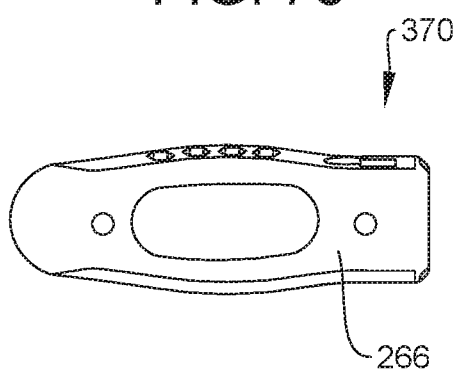
FIG. 76
FIG. 77

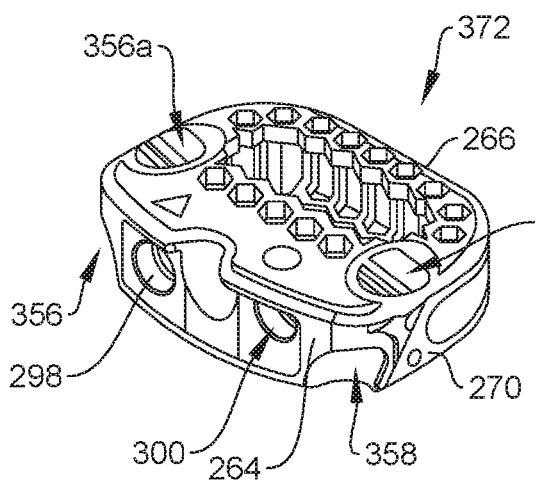
FIG. 78
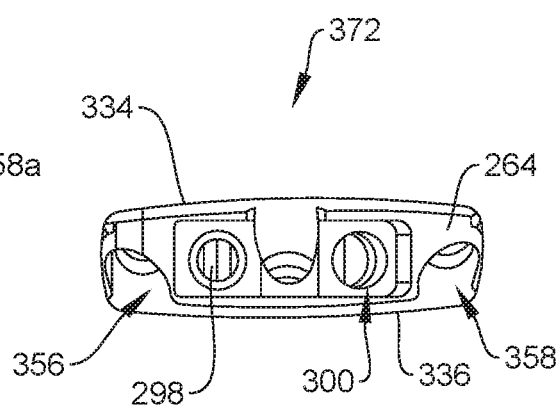
FIG. 79
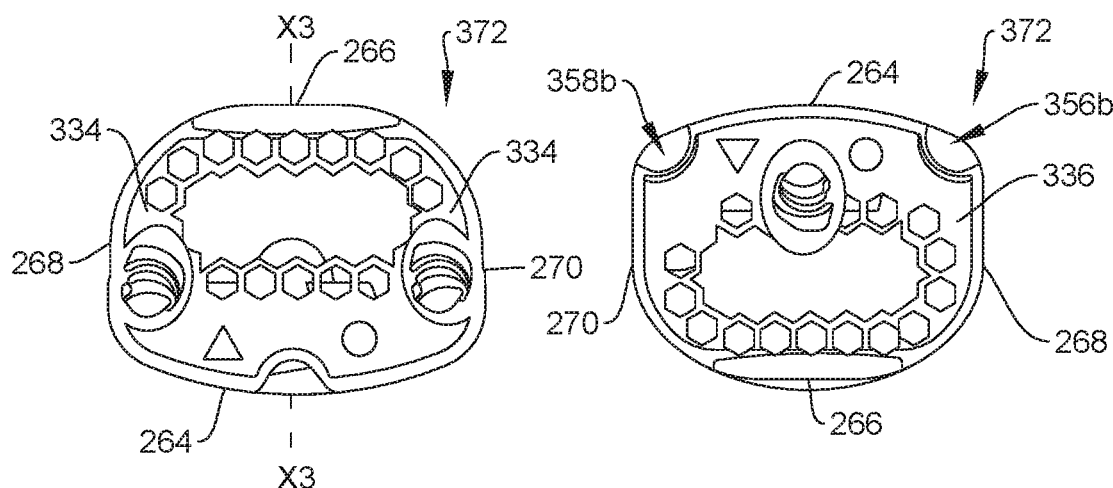
FIG. 80
FIG. 81
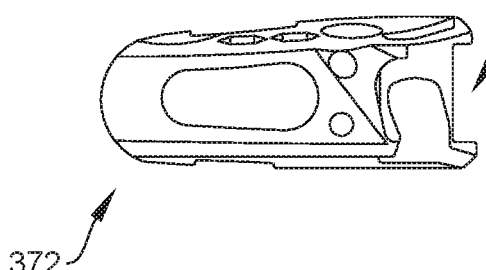
FIG. 82
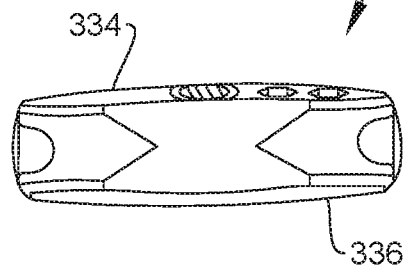
FIG. 83

SPINAL IMPLANT SYSTEM AND METHOD

CROSS REFERENCE TO RELATED APPLICATIONS

This application is a divisional application of U.S. patent application Ser. No. 16/395,928, filed Apr. 26, 2019, which is expressly incorporated by reference herein, in its entirety.

TECHNICAL FIELD

The present disclosure generally relates to medical devices for the treatment of musculoskeletal disorders, and more particularly to a spinal implant system including an implant and an instrument configured to deliver the implant during a surgical procedure.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, such as, for example, bone fasteners, plates and interbody devices can be used to provide stability to a treated region. For example, during surgical treatment, interbody implants can be delivered to a surgical site for fixation with bone to immobilize a joint. The bone fasteners extend through a plate and/or an interbody device and into bone to fix at least a portion of the plate and/or the interbody device to the bone. This disclosure describes an improvement over these prior art technologies.

SUMMARY

In one embodiment, in accordance with the principles of the present disclosure, a surgical instrument comprises a sleeve extending along a longitudinal axis between opposite proximal and distal ends. An inner surface of the sleeve defines a passageway. The distal end defines an engagement portion. The engagement portion comprises an engagement surface extending from a first end to an opposite second end. The engagement portion comprises a peg extending outwardly from the first end. The engagement portion comprises an opening extending through the second end. The opening is in communication with the passageway. A knob is coupled to the proximal end of the sleeve. A shaft comprises a proximal end and an opposite distal end. The distal end of the shaft comprises a mating portion. The mating portion extends through the opening. The proximal end of the shaft is coupled to the knob. The knob is rotatable relative to the sleeve to rotate the shaft relative to the sleeve.

In one embodiment, in accordance with the principles of the present disclosure, a surgical system includes a spinal implant comprising opposite first and second vertebral engaging surfaces. The implant comprises opposite posterior and anterior surfaces each extending from the first vertebral engaging surface to the second vertebral engaging surface. The anterior surface comprises spaced apart first and second cavities. A surgical instrument comprises a sleeve extending along a longitudinal axis between opposite proximal and distal ends. An inner surface of the sleeve defines a passageway. The distal end defines an engagement portion. The engagement portion comprises an engagement surface extending from a first end to an opposite second end. The engagement portion comprises a peg extending outwardly from the first end. The peg is positioned in the first cavity. The engagement portion comprises an opening extending through the second end. The opening is in communication with the passageway. A knob is coupled to the proximal end of the sleeve. A shaft comprises a proximal end and an opposite distal end. The distal end of the shaft comprises a mating portion. The proximal end of the shaft is coupled to the knob. The knob is rotatable relative to the sleeve to translate the shaft relative to the sleeve between a first orientation in which the mating portion is positioned within the passageway and a second orientation in which the mating portion mates with a mating surface of the second cavity.

In one embodiment, in accordance with the principles of the present disclosure, a surgical instrument comprises an outer sleeve extending along a longitudinal axis between opposite proximal and distal ends. An inner surface of the sleeve defines a passageway. The distal end defines an engagement portion. The engagement portion comprises an engagement surface extending from a first end to an opposite second end. The first end comprises a first cavity in communication with the passageway. The second end comprises a second cavity. An inner sleeve is rotatably positioned within the passageway. The inner sleeve comprises an outer surface that engages the inner surface of the outer sleeve and an inner surface defining a female thread form. A knob is coupled to the proximal end of the sleeve. The knob is rotatable relative to outer sleeve to rotate the inner sleeve relative to the outer sleeve.

In one embodiment, in accordance with the principles of the present disclosure, a spinal implant includes a body comprising opposite first and second end walls and opposite first and second side walls. The side walls each extend from the first end wall to the second end wall. A first cap is coupled to top ends of the walls. A second cap is coupled to bottom ends of the walls. The implant comprising an opening extending through the caps such that the first cap defines a first ledge extending from the walls to the opening and the second cap defines a second ledge extending from the walls to the opening.

In one embodiment, in accordance with the principles of the present disclosure, a spinal implant includes a body comprising opposite first and second end walls and opposite first and second side walls. The side walls each extend from the first end wall to the second end wall. The first side wall defines a first window. The second side wall define a second window. Inner surfaces of the walls define a cavity. A core is positioned in the cavity such that the core is viewable through the windows. A first cap is coupled to top ends of the walls. A second cap is coupled to bottom ends of the walls. The implant comprises an opening extending through the caps such that the first cap defines a first ledge extending from the walls to the opening and the second cap defines a second ledge extending from the walls to the opening.

In one embodiment, in accordance with the principles of the present disclosure, a spinal implant includes a body comprising opposite first and second end walls and opposite first and second side walls. The side walls each extend from the first end wall to the second end wall. The first side wall defines a first window. The second side wall defines a second window. Inner surfaces of the walls define a cavity. A core is positioned in the cavity such that the core is viewable through the windows. The core has a lattice configuration. A first cap is coupled to top ends of the walls. A second cap is coupled to bottom ends of the walls. The implant comprises an opening extending through the caps such that the first cap defines a first ledge extending from the walls to the opening and the second cap defines a second ledge extending from the walls to the opening. The ledges each extend circumferentially about the opening. Bone graft is positioned between the first ledge and the second ledge. The caps each include a plurality of apertures. The apertures have a hexagonal configuration. The core is fused together with the body and the caps. The cavity has a maximum diameter that is greater than a maximum diameter of the opening.

BRIEF DESCRIPTION OF THE DRAWINGS

The present disclosure will become more readily apparent from the specific description accompanied by the following drawings, in which:

FIG. 42 is a perspective view of one embodiment of the second component of the spinal system shown in FIG. 1, in accordance with the principles of the present disclosure;

FIG. 43 is a front view of the second component shown in FIG. 42;

FIG. 44 is a top view of the second component shown in FIG. 42;

FIG. 45 is a bottom view of the second component shown in FIG. 42;

FIG. 46 is a side view of the second component shown in FIG. 42;

FIG. 47 is a rear view of the second component shown in FIG. 42;

FIG. 66 is a perspective view of one embodiment of the second component of the spinal system shown in FIG. 1, in accordance with the principles of the present disclosure;

FIG. 67 is a front view of the second component shown in FIG. 66;

FIG. 68 is a top view of the second component shown in FIG. 66;

FIG. 69 is a bottom view of the second component shown in FIG. 66;

FIG. 70 is a side view of the second component shown in FIG. 66;

FIG. 71 is a rear view of the second component shown in FIG. 66;

FIG. 72 is a perspective view of one embodiment of the second component of the spinal system shown in FIG. 1, in accordance with the principles of the present disclosure;

FIG. 73 is a front view of the second component shown in FIG. 72;

FIG. 74 is a top view of the second component shown in FIG. 72;

FIG. 75 is a bottom view of the second component shown in FIG. 72;

FIG. 76 is a side view of the second component shown in FIG. 72;

FIG. 77 is a rear view of the second component shown in FIG. 72;

FIG. 78 is a perspective view of one embodiment of the second component of the spinal system shown in FIG. 1, in accordance with the principles of the present disclosure;

FIG. 79 is a front view of the second component shown in FIG. 78;

FIG. 80 is a top view of the second component shown in FIG. 78;

FIG. 81 is a bottom view of the second component shown in FIG. 78;

FIG. 82 is a side view of the second component shown in FIG. 78; and

FIG. 83 is a rear view of the second component shown in FIG. 78.

DETAILED DESCRIPTION

Figure 1:
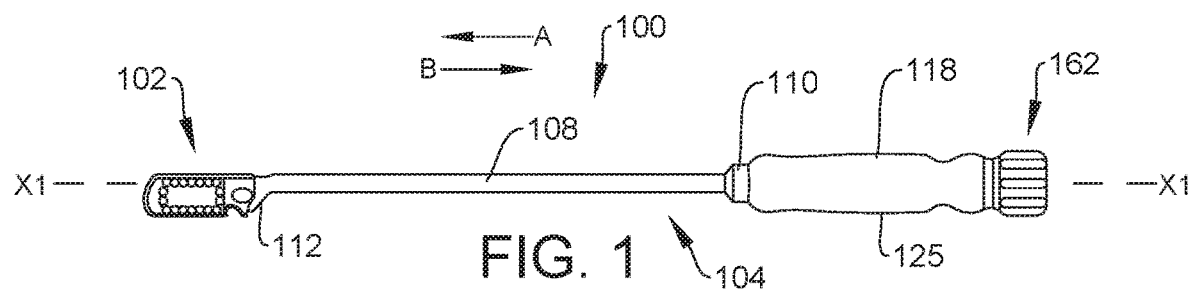
FIG. 1 is a side view of first and second components of a spinal system, in accordance with the principles of the present disclosure.

The exemplary embodiments of the spinal system and related methods of use disclosed are discussed in terms of medical devices for the treatment of musculoskeletal disorders and more particularly, in terms of a surgical system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system includes a spinal implant having graft containment overhangs. The overhangs grip the graft to prevent graft loss during impaction. In some embodiments, the implant includes a porous lattice optimized for strength, while allowing a large graft volume to be disposed between the graft containment overhangs. In some embodiments, the implant includes screw pockets that are completely enclosed to prevent bone screws that are inserted into the pockets from interfering with graft, and vice versa.

In some embodiments, the implant includes a solid body having edges, markers, a nose and inserter and bone screw attachment geometry. The implant includes a core configured to be positioned within a cavity of the body. The core includes a structural lattice that reduces stiffness and opacity, while maintaining strength. The implant includes top and bottom caps that are each coupled to the body when the core is positioned within the body. In some embodiments, at least one of the caps includes a trabecular like structure having an interconnected porosity that is optimized for ingrowth and ongrowth. In some embodiments, the caps are fused with the core and the body to prevent delamination of the implant. In some embodiments, the structural lattice of the core is a diamond lattice that is produced by 3D printing to provide exceptional buildability, exceptional strength, reduced internal stress, and fit within a variety of spinal implant type geometries.

The surgical system includes an inserter configured to insert the implant between vertebrae during a surgical procedure using a selected surgical approach and/or at a selected angle. For example, in some embodiments, a single implant can be inserted between vertebrae using four different surgical approaches (e.g., an approach for Anterior Lumbar Interbody Fusion (ALIF), an approach for Oblique Lateral Interbody Fusion at L5-S1 (OLIF 5-1), an approach for Oblique Lateral Interbody Fusion at L2-L5 (OLIF 2-5), and an approach for Direct Lateral Interbody Fusion (DLIF)) with a single inserter, as discussed herein. Indeed, the inserter includes attachment geometry that is low profile, suitable for navigation, and allows multiple insertion angles and designs. That is, a single inserter may be used to deliver several different implants to a target site using different surgical approaches and/or at different angles. In some embodiments, the inserter includes a ratchet mechanism that prevents undesired disengagement of the implant from the inserter before and during any impaction.

In some embodiments, the implant includes an arced surface configured for engagement with an arced surface of the inserter to couple the inserter to the implant. In some embodiments, a peg and a shaft of the inserter are positioned within cavities, such as, for example, threaded cavities of the implant when the arced surface of the inserter engages the arced surface of the implant. Lines that intersect end points of the arced surface of the implant and an arced center of the arced surface of the implant can be flipped. As such, if the implant is attached to a handle of the inserter, the given angle of attachment will change. Indeed, the arced surface of the implant can be flipped after the inserter is coupled to the implant to couple the inserter to the implant such that the insertion angle of the inserter changes. In some embodiments, the peg and the shaft of the inserter are configured to be positioned in the threaded cavities of the implant before and after the inserter is flipped. In some embodiments, the geometry of an implant configured for use in an OLIF 5-1 procedure and the geometry of an implant configured for use in an OLIF 2-5 procedure allow both implants to be inserted using a single inserter, thus allowing for further instrument consolidation. That is, the arced surface of the single inserter can match the arced surface of the implant configured for use in an OLIF 5-1 procedure and the arced surface of the implant configured for use in an OLIF 2-5 procedure. The peg and the rod of the inserter are positioned in the threaded cavities of the implant configured for use in an OLIF 5-1 when the arced surface of the inserter engages the arced surface of the implant configured for use in an OLIF 5-1 procedure and the rod and peg of the inserter are positioned in the threaded cavities of the implant configured for use in an OLIF 2-5 procedure when the arced surface of the inserter engages the arced surface of the implant configured for use in an OLIF 2-5 procedure. In some embodiments, the peg of the inserter provides connection strength between the inserter and the implant.

In some embodiments, the inserter engages the implant such that access to outer bone screws that extend through the implant are accessible when the inserter engages the implant, as discussed herein. In some embodiments, the inserter includes flat contacts that engage a surface of the implant while the rod and peg of the inserter are positioned in the threaded cavities of the implant to couple the inserter to the implant.

In some embodiments, the features of the inserter and the features of the implants are reversed. For example, the implant can include one or a plurality of pegs, such as, for example, threaded pegs that extend outwardly from a body of the implant. The pegs may be received within cavities of the inserter. An arced surface of the inserter engages an arced surface of the implant when the pegs are received within the cavities to couple the inserter to the implant. In some embodiments, this allows use of larger threads. In some embodiments, a sleeve including a female thread form is rotatably positioned within one of the cavities of the inserter such that the female thread form mates with a male thread form of one of the pegs of the inserter to couple the inserter to the implant, as discussed herein.

In some embodiments, the arced surface of the inserter and the arced surface of the implant can be reversed. For example, in some embodiments, the inserter can include a concavely curved surface that engages a convexly curved surface of the implant to couple the inserter to the implant. Alternatively, the inserter can include a convexly curved surface that engages a concavely curved surface of the implant to couple the inserter to the implant.

In some embodiments, the arced surface of the implant can include two or more cavities configured for disposal of the peg of the inserter and the shaft of the inserter. For example, in one embodiment, the implant includes two cavities configured for disposal of the peg of the inserter and the shaft of the inserter. In one embodiment, the implant includes three cavities configured for disposal of the peg of the inserter and the shaft of the inserter such that one of the cavities is empty or unoccupied when the peg of the inserter and the shaft of the inserter are disposed in the two other cavities. This allows the implant to be disposed at three different angles relative to the inserter, as discussed herein. In some embodiment, the cavities are all positioned along the same arc path of the implant, the arc path of the implant coinciding with an arc center of the inserter. In some embodiments, at least one of the cavities is threaded.

In some embodiments, the arced surface of the inserter includes a central cutout configured for disposal of a tab, such as, for example, a plate that is coupled to the implant such that the inserter can be used to insert the implant with the plate attached to the implant, as discussed herein. In some embodiments, the arced surface of the inserter includes a central cutout configured to allow access to an intrinsic screw that extends into or through the implant such that the intrinsic screw can be rotated relative to the implant while the intrinsic screw extends into or through the implant and the inserter is attached to the implant.

In some embodiments, the inserter includes a ratchet knob comprising a first member or plate, such as, for example, a floating plate that engages grooves on a second plate of the inserter. In particular, a spring pushes the floating plate such that extensions of the floating plate engage the grooves on the second plate to prevent undesired loosening of the implant upon impaction. As a user rotates the ratchet knob, the float plate rides in the grooves, creating resistance similar to a ratchet, as discussed herein.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including implants, related components and methods of employing the surgical system in accordance with the principles of the present disclosure. Alternate embodiments are also disclosed. Reference is made in detail to the exemplary embodiments of a surgical system 100, which are illustrated in the accompanying figures.

The components of surgical system 100 can be fabricated from biologically acceptable materials suitable for medical applications, including metals, synthetic polymers, ceramics and bone material and/or their composites. For example, the components of surgical system 100, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 100 may have material composites, including the above materials, to achieve various desired characteristics such as strength, rigidity, elasticity, compliance, biomechanical performance, durability and radiolucency or imaging preference. The components of surgical system 100, individually or collectively, may also be fabricated from a heterogeneous material such as a combination of two or more of the above-described materials. The components of surgical system 100 may be monolithically formed, integrally connected or include fastening elements and/or instruments, as described herein.

Surgical system 100 is employed, for example, with a fully open surgical procedure, a minimally invasive procedure including percutaneous techniques, and mini-open surgical techniques to deliver and introduce instrumentation and/or one or more spinal implants, such as, for example, one or more components of a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 2:
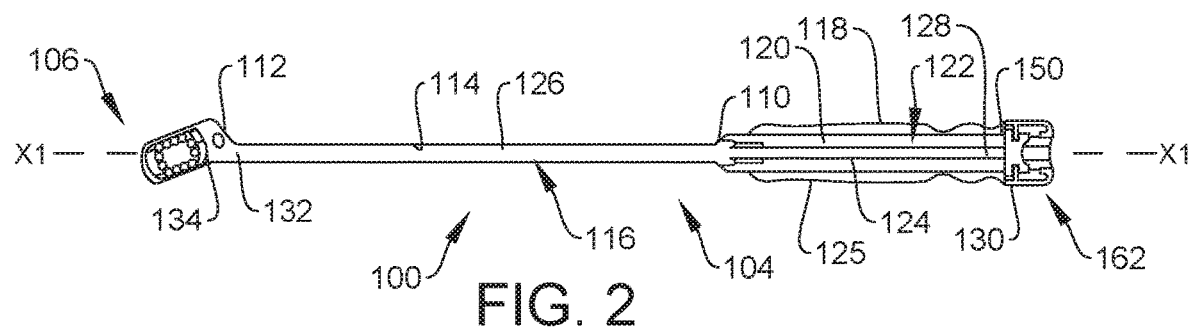
FIG. 2 is a side, cross-sectional view of the first component of the spinal system shown in FIG. 1 coupled to one embodiment of a second component of the spinal system, in accordance with the principles of the present disclosure.
Figure 3:
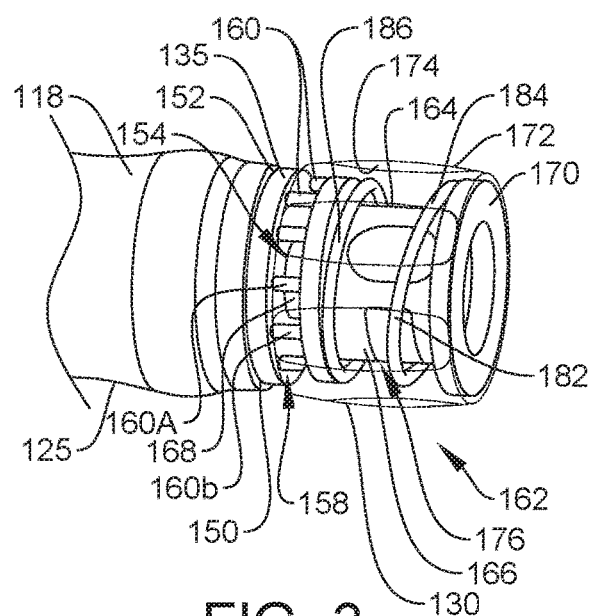
FIG. 3 is a perspective, breakaway view, in part phantom, of the first component of the spinal system shown in FIG. 1.

Surgical system 100 includes an implant, such as, for example, a spinal implant 102 and an instrument, such as, for example, a surgical instrument 104 configured to insert implant 102 into an intervertebral space defined by adjacent vertebrae, as discussed herein. In some embodiments, instrument 104 may be used to insert implant 102 and/or other implants that are similar to implant 102 into an intervertebral space defined by adjacent vertebrae. For example, instrument 104 is shown in FIG. 1 with instrument 104 coupled to implant 102 to allow instrument 104 to insert implant 102 into an intervertebral space. Instrument 104 is shown in FIG. 2 with instrument coupled to an implant 106 that is similar to implant 104 to allow instrument 104 to insert implant 106 into an intervertebral space. However, it should be understood that instrument 104 may be used to insert implants in addition to implants 102, 106 into an intervertebral space, as discussed herein.

Instrument 104 includes a sleeve 108 extending along a longitudinal axis X1 between a proximal end 110 and an opposite distal end 112. An inner surface 114 of sleeve 108 defines a passageway 116. Passageway 116 is coaxial with axis X1. End 110 is coupled to a handle 118 of instrument 104 such that a body 125 of handle 118 is fixed relative to sleeve 108. In some embodiments, handle 118 has a maximum diameter that is greater than a maximum diameter of sleeve 108 to facilitate gripping of handle 118 by a hand of a medical practitioner, for example. In some embodiments, handle 118 includes gripping features, such as, for example, indentations and/or protrusions configured to facilitate gripping. An inner surface 120 of handle 118 defines a channel 122 that is coaxial with passageway 116 and axis X1. Channel 122 is in communication with passageway 116 such that a shaft 124 of instrument 104 extends through channel 122 and into passageway 116. Shaft 124 is rotatable relative to sleeve 108 and handle 118 about axis X1, as discussed herein. In some embodiments, passageway 116 has a diameter that is slightly greater than a diameter of shaft 124 such that an outer surface 126 of shaft 124 directly engages surface 114 of sleeve 108 when shaft 124 is positioned within passageway 116. It is envisioned that the engagement of surface 126 with surface 114 maintains the orientation of shaft 124 relative to sleeve 108 and/or handle 118 such that shaft 124 remains coaxial with axis X1 when shaft 124 is positioned within passageway 116. That is, the engagement of surface 126 with surface 114 prevents shaft 124 from extending at an acute angle relative to axis X1 when shaft 124 is positioned within passageway 116. In some embodiments, passageway 116 has a diameter that is greater than a diameter of shaft 124 such that surface 126 of shaft 124 is spaced apart from surface 114 of shaft 124 when sleeve 108 is positioned within passageway 116. In some embodiments, passageway 116 has a uniform diameter along an entire length of passageway 116 and/or channel 122 has a uniform diameter along an entire length of channel 122. In some embodiments, passageway 116 and/or channel 122 may be variously shaped, such as, for example, circular, oval, oblong, triangular, square, polygonal, irregular, uniform, non-uniform, offset, staggered, undulating, arcuate, variable and/or tapered.

A proximal end 128 of shaft 124 is coupled to a knob 130 and an opposite distal end 132 of shaft 124 includes a mating surface 132, such as, for example, a male thread form configured to engage an implant to couple the implant to shaft 124. In particular, the male thread form of mating surface 132 is configured to mate with a female thread form of an implant to couple the implant to shaft 124, as discussed herein. Proximal end 128 of shaft 124 is fixed to knob 130 such that rotation of knob 130 about axis X1 also rotates shaft 124 about axis X1, as discussed herein. In some embodiments, knob 130 is integrally and/or monolithically formed with shaft 124. In some embodiments, shaft 124 is welded to knob 130. It is envisioned that shaft 124 can be cannulated or non-cannulated, depending upon the requirements of a particular application.

Distal end 112 of sleeve 108 defines an engagement portion 136 comprising an engagement surface 138 extending from a first end 140 to an opposite second end 142. In some embodiments, engagement portion 136 comprises a peg 144 extending outwardly from end 140 and an opening 146 extending through end 136. In some embodiments, engagement portion 136 does not include a peg or any other structure extending from engagement surface 138 and engagement portion 136 includes only opening 146, wherein opening 146 can be variously positioned relative to engagement surface 138. Opening 146 is in communication with passageway 116 such that shaft 124 can be translated axially along axis X1 within passageway 116 to move mating surface 134 through opening 146 for engagement with an implant, as discussed herein. Peg 144 is permanently fixed relative to surface 138. In some embodiments, opening 146 is coaxial with passageway 116 and axis X1 and peg 144 extends at an acute angle relative to axis X1. Peg 144 has a solid configuration that is free of any gaps or openings to provide strength and rigidity to peg 144. In some embodiments, peg 144 has a beveled tip 148 to facilitate insertion of peg 144 into a cavity of an implant, for example, to couple instrument 104 to the implant, as discussed herein. In some embodiments, the beveled tip is biased toward one side. In some embodiments, peg 144 is cone shaped. In some embodiments, peg 144 is cylindrical. In some embodiments, peg 144 has a radius for smooth transition. In some embodiments, peg 144 is variously shaped, such as, for example, oval, oblong, triangular, square, polygonal, irregular, uniform, non-uniform, offset, staggered, undulating, arcuate, variable and/or tapered.

Figure 4:
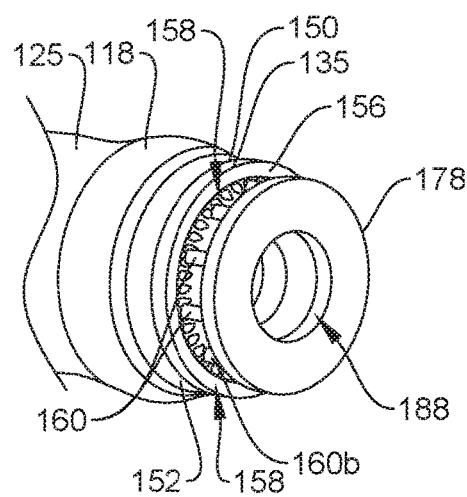
FIG. 4 is a perspective, breakaway view of the first component of the spinal system shown in FIG. 1, with parts separated.
Figure 4A:
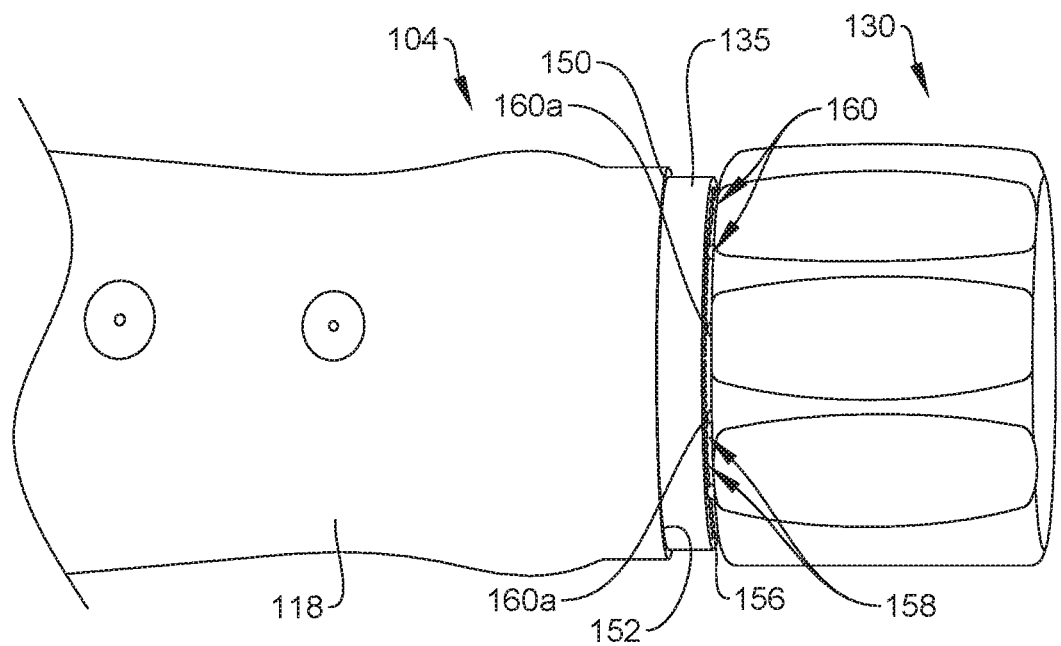
FIG. 4A is a side, breakaway view of the first component of the spinal system shown in FIG. 1.
Figure 4B:
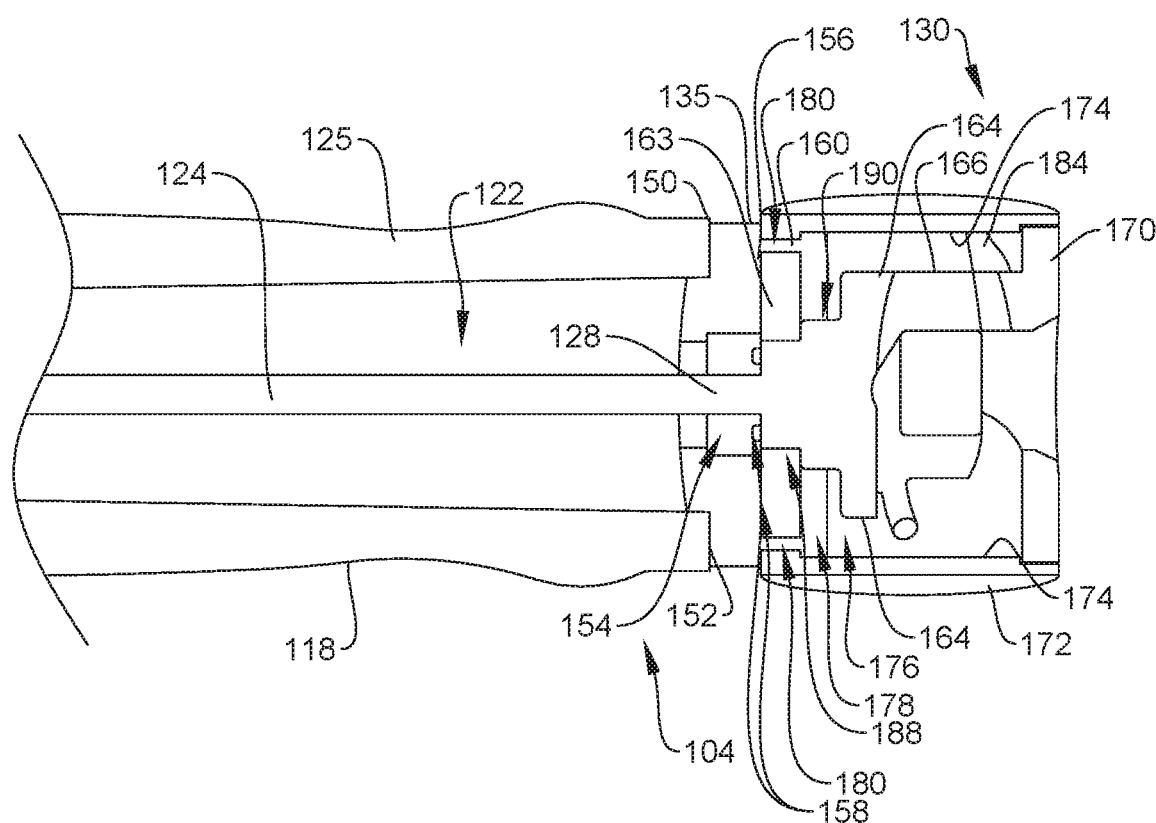
FIG. 4B is a side, cross-sectional, breakaway view of the first component of the spinal system shown in FIG. 1.
Figure 5:
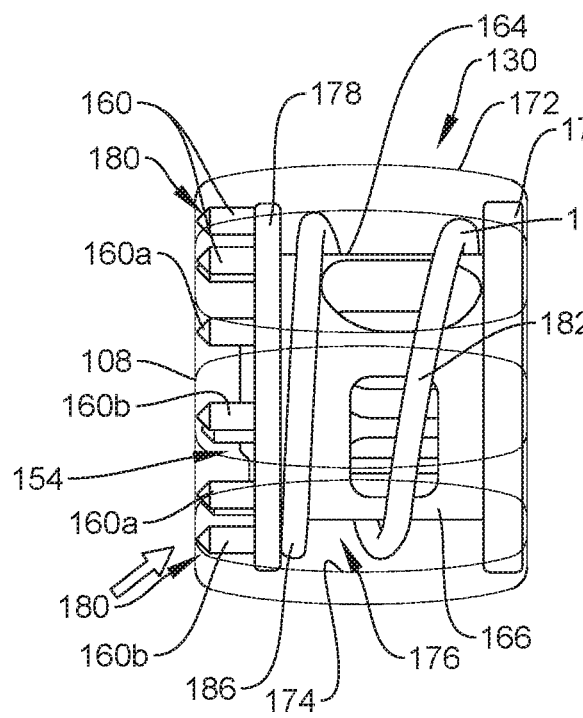
FIG. 5 is a side view, in part phantom, of the first component of the spinal system shown in FIG. 1.
Figure 6:
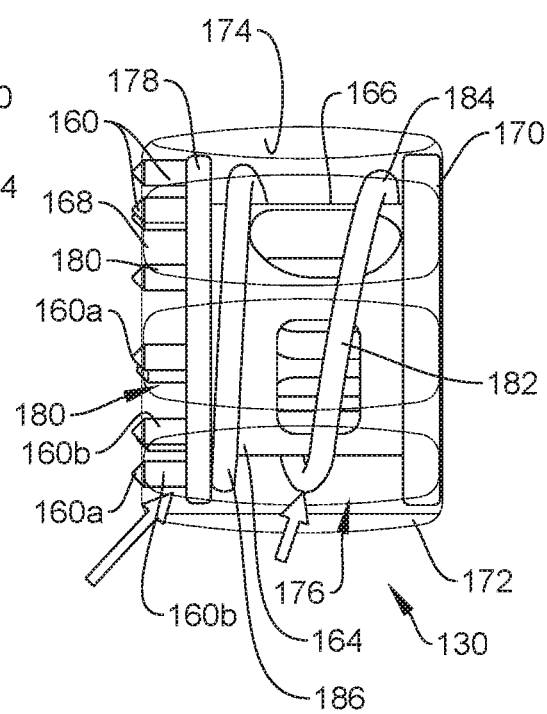
FIG. 6 is a side view, in part phantom, of the first component of the spinal system shown in FIG. 1.
Figure 7:
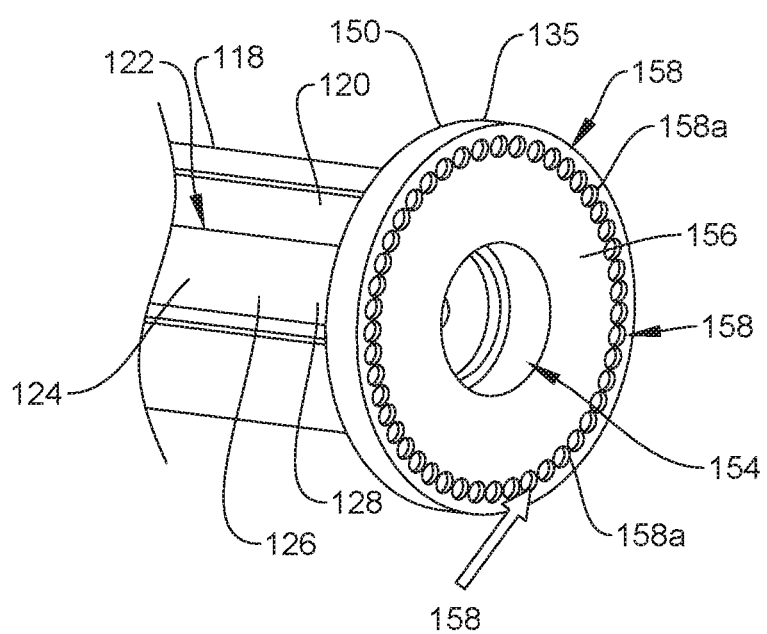
FIG. 7 is a perspective, breakaway view of the first component of the spinal system shown in FIG. 1.

Handle 118 includes a member, such as, for example, a plate 135 that is coupled to body 125 of handle 118 such that plate 135 is fixed relative to body 125. Plate 135 has a diameter that is greater than a diameter of channel 122. An end surface 150 of plate 135 directly engages an end surface 152 of body 125 to couple plate 135 to body 125. In some embodiments, end surface 152 is integrally and/or monolithically formed with end surface 150. In some embodiments, end surface 152 is welded to end surface 150 or otherwise coupled to end surface 150 to fix plate 135 relative to body 125. Plate 135 includes an aperture 154 extending through a thickness of plate 135 that is defined by a distance between end surface 150 and an opposite end surface 156. Aperture 154 is coaxial with shaft 124 and axis X1. Proximal end 128 of shaft 124 extends through aperture 154, as best shown in FIG. 4B. Plate 135 includes a plurality of spaced apart grooves, such as, for example, openings 158 that are positioned radially about aperture 154. That is, openings 158 extend circumferentially about aperture 154. Openings 158 extend parallel to axis X1 and are each configured for disposal of an extension 160 of knob 130 to prevent rotation of shaft 124 relative to handle 118 and sleeve 108 about axis X1, as discussed herein.

In some embodiments, openings 158 include a bevel 158*a* to facilitate insertion of extensions 160 into openings 158. That is, tapered bevels 158*a* of openings 158 that extend into end surface 156 have a greater diameter than cylindrical second portions of openings 158 that are positioned between end surface 156 and end surface 150. In some embodiments, extensions 160 included tapered tips 160*a* configured to facilitate insertion of extensions 160 into openings 158. In some embodiments, tips 160*a* terminate in a sharp point. In some embodiments, at least one of openings 158 extends through end surface 156 without extending through end surface 150. In some embodiments, at least one of openings 158 extends through end surface 156 and end surface 150. In some embodiments, plate 135 has a uniform thickness. In some embodiments, aperture 154 and/or openings 158 variously shaped, such as, for example, circular, oval, oblong, triangular, square, polygonal, irregular, uniform, non-uniform, offset, staggered, undulating, arcuate, variable and/or tapered.

Knob 130 includes a hub 164 comprising a cylindrical body 166. Proximal end 128 of shaft 124 is coupled to a distal end of hub 164 such that end 128 is fixed relative to hub 164, as best shown in FIG. 4B. In some embodiments, end 128 is integrally and/or monolithically formed with hub 164. In some embodiments, end 128 is welded to hub 164 such that rotation of hub 164 also rotates shaft 124. A gripping portion 172 of knob 130 includes a disc 170 that is fixed to hub 164. In some embodiments, disc 170 is integrally and/or monolithically formed with gripping portion 172 such that rotation of gripping portion 172 also rotates disc 170. In some embodiments, disc 170 is welded to gripping portion 172. In some embodiments, disc 170 is integrally and/or monolithically formed with hub 164 such that rotation of gripping portion 172 also rotates disc 170 and hub 164. In some embodiments, disc 170 is welded to hub 164. Gripping portion 172 further includes a member, such as, for example, a plate 168 that is fixed to hub 164, a member, such as, for example, a plate 170 and gripping portion 172. In some embodiments, plate 168 is integrally and/or monolithically formed with hub 164, plate 170 and/or gripping portion 172 such that rotation of plate 168 also rotates hub 164. In some embodiments, plate 168 is welded to hub 164.

An inner surface 174 of gripping portion 172 defines a cavity 176. A floating member or plate, such as, for example, a plate 178 is movably disposed in cavity 176. Extensions 160 extend outwardly from a distal end of plate 178. Plate 168 includes an aperture 188 and plate 178 includes an aperture 190. Apertures 188, 190 are each coaxial with axis X1 such that apertures 188, 190 are aligned with aperture 154 of plate 135 and end 128 of shaft 124 extends through apertures 154, 188, 190 for connection with hub 164.

Extensions 160 are configured to move through grooves, such as, for example, openings 180 in plate 178 and into openings 158 of plate 135. In particular, knob 130 is rotatable between a first configuration in which extensions 160 are spaced apart from openings 158 or only tips 160*a* of extensions 160 are positioned within openings 158 and a second configuration in which extensions 160 are disposed in the openings 158. That is, extensions 160 are spaced apart from openings 158 or are only partially positioned within openings 158 when knob 130 is in the first configuration and extensions 160 are fully disposed in the openings 158 when knob 130 is in the second configuration. In some embodiments, cylindrical portions 160*b* of extensions 160 are positioned in openings 158 when extensions 160 are fully disposed in the openings 158 and knob 130 is in the second configuration. Cylindrical portions 160*b* of extensions 160 are positioned in openings 180 and tips 160*a* of extensions 160 are positioned outside of openings 180 when knob 130 is in the first configuration and the second configuration. Knob 130 is rotatable relative to sleeve 108 and handle 118 when knob 130 is in the first configuration. Knob 130 is prevented from rotating relative to 108 and handle 118 when knob 130 is in the second configuration. As such, shaft 124 is rotatable relative to sleeve 108 and handle 118 when knob 130 is in the first configuration and shaft 124 is prevented from rotating relative to sleeve 108 and handle 118 when knob 130 is in the second configuration. Indeed, when only tips 160*a* of extensions 160 are positioned within openings 158, the tapered configuration of tips 160*a* allows tips 160*a* to move in and out of adjacent openings 158 as knob 130 is rotated relative to sleeve 108 and handle 118. When extensions 160 are inserted further into openings 158 such that cylindrical portions 160*b* of extensions are positioned within openings 158, knob 130*s* prevented from being rotated relative to sleeve 108 and handle 118 since extensions 160 are prevented from moving from one of openings 158 to another one of openings 158.

In some embodiments, knob 130 is biased to the second configuration by a biasing member, such as, for example, a spring 182 that is positioned about hub 164. That is, spring 182 has a first end 184 that directly engages disc 170 and an opposite second end 186 that directly engages plate 178 to move plate 178 away from disc 170 such that extensions 160 move through openings 180 and into openings 158. In some embodiments, the force exerted by spring 182 to plate 178 is sufficient to move knob 130 from the first configuration to the second configuration. In some embodiments, the force exerted by spring 182 to plate 178 is insufficient to move knob 130 from the first configuration to the second configuration. For example, in one embodiment, knob 130 will remain in the first configuration unless and until mating surface 134 mates with a mating surface of an implant, such as, for example, implant 104 or implant 106. When mating surface 134 mates with the mating surface of the implant, rotation of knob 130 relative to sleeve 108 and handle 118 causes shaft 124 to translate axially relative to sleeve 108 and handle 118. As shaft 124 translates axially relative to sleeve 108 and handle 118, knob 130 translates axially relative to plate 135 to move knob 130 toward plate 135 such that extensions 160 are fully disposed in the openings 158 and knob 130 is in the second configuration.

In assembly, operation and use, surgical system 100, similar to the systems and methods described herein, is employed with a surgical procedure for treatment of a spinal disorder affecting a section of a spine of a patient, as discussed herein. The components of surgical system 100 are employed with a surgical procedure for treatment of a condition or injury of an affected section of the spine, such as, for example, vertebrae.

In use, to treat a selected section of vertebrae, a medical practitioner obtains access to a surgical site in any appropriate manner, such as through incision and retraction of tissues. In some embodiments, surgical system 100 can be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, the particular surgical procedure can be performed for treating the spine disorder.

Figure 11:
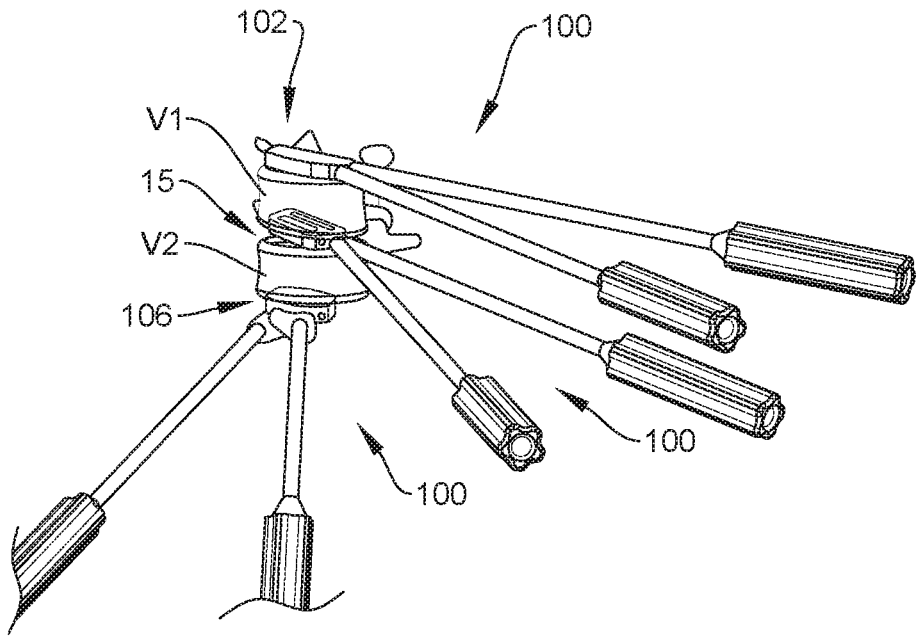
FIG. 11 is a plan view showing the first and second components of the spinal system shown in FIG. 1 disposed with vertebrae, with the first and second components of the spinal system shown in FIG. 1 in various orientations.

An incision is made in the body of a patient and a cutting instrument creates a surgical pathway for implantation of components of surgical system 100. A preparation instrument can be employed to prepare tissue surfaces of vertebrae as well as for aspiration and irrigation of a surgical region. Instrument 104 is coupled to an implant, such as, for example, an implant 192, that is configured to be inserted into a target site, such as, for example, an intervertebral space IS between a first vertebra V1 and a second vertebra V2, as shown in FIG. 11. As shown in FIGS. 14-17, implant 192 includes opposite first and second vertebral engaging surfaces 194, 196. Vertebral engaging surface 194 is configured to engage an endplate of vertebra V1 and vertebral engaging surface 196 is configured to engage an endplate of vertebra V2. Implant 192 includes a posterior surface 198 and an anterior surface 200 opposite surface 198. Surfaces 198, 200 each extend from surface 194 to surface 196. Surface 200 defines a cavity 202 and a cavity 204 that is spaced apart from cavity 202. Cavity 202 includes a female thread form 202a and cavity 204 includes a female thread form 204a.

Figure 15:
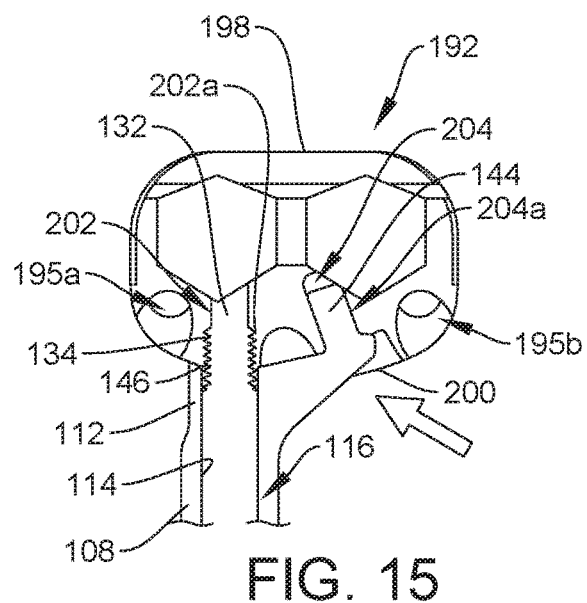
FIG. 15 is a side, breakaway, cross-sectional view of the second component shown in FIG. 14 coupled to the first component of the spinal system shown in FIG. 1.

In one embodiment, implant 192 is configured for use in an ALIF procedure. Implant 192 is connected to instrument 104 by inserting peg 144 into cavity 204 such that opening 146 is aligned with cavity 202, as shown in FIG. 15. Knob 130 in the first configuration when peg 144 is inserted into cavity 204 such that knob 130 is able to translate shaft 124 relative to sleeve 108 and handle 118 along axis X1 in the direction shown by arrow A in FIG. 1 and/or the direction shown by arrow B in FIG. 1. Knob 130 is translated relative to sleeve 108 and handle 118 along axis X1 in the direction shown by arrow A in FIG. 1 to move shaft 124 from a first position in which mating surface 134 is positioned entirely within passageway 116 to a second position in which mating surface 134 extends through opening 146 and into cavity 202, as shown in FIG. 15. Knob 130 is rotated about axis X1 in a first rotational direction, such as, for example, clockwise as knob 130 is translated relative to sleeve 108 and handle 118 along axis X1 in the direction shown by arrow A in FIG. 1 such that the male thread form of mating surface 134 mates with female thread form 202a. When the male thread form of mating surface 134 mates with female thread form 202a, further rotation of knob 130 relative to sleeve 108 and handle 118 in the first rotational direction causes shaft 124 to translate axially relative to sleeve 108 and handle 118 in the direction shown by arrow A in FIG. 1. Because knob 130 is in the first configuration, knob 130 is rotatable relative to sleeve 108 and handle 118 to translate shaft 124 axially relative to sleeve 108 and handle 118. As shaft 124 translates axially relative to sleeve 108 and handle 118 in the direction shown by arrow A in FIG. 1, knob 130 translates axially relative to plate 135 in the direction shown by arrow A in FIG. 1 to move knob 130 toward plate 135 such that extensions 160 are fully disposed in the openings 158 and knob 130 is in the second configuration.

Implant 192 is guided into intervertebral space IS using instrument 104. Once implant 192 is selectively positioned within intervertebral space IS knob 130 is rotated relative to sleeve 108 and handle 118 about axis X1 in a second rotational direction, such as, for example, counterclockwise. Knob 130 is rotated relative to sleeve 108 and handle 118 about axis X1 in the second rotational direction with a force sufficient to overcome the force of spring 182 to move knob 130 from the second configuration to the first configuration. As knob 130 moves from the second configuration to the first configuration, shaft 124 moves from the second position in which mating surface 134 extends through opening 146 and into cavity 202 to the first position in which mating surface 134 is positioned entirely within passageway 116. Peg 144 is removed from cavity 204 when shaft 124 is in the first position.

Upon completion of a procedure, as described herein, the surgical instruments, assemblies and non-implanted components of surgical system 100 are removed and the incision(s) are closed. One or more of the components surgical system 100 can be made of radiolucent materials such as polymers. Radiomarkers may be included for identification under x-ray, fluoroscopy, CT or other imaging techniques. In some embodiments, surgical system 100 may include one or a plurality of spinal rods, plates, connectors and/or bone fasteners for use with a single vertebral level or a plurality of vertebral levels.

In some embodiments, one or more bone screws, as described herein, may be engaged with tissue in various orientations, such as, for example, series, parallel, offset, staggered and/or alternate vertebral levels. In some embodiments, one or more of the bone screws may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, surgical system 100 includes an agent, which may be disposed, packed, coated or layered within, on or about the components and/or surfaces of surgical system 100. In some embodiments, the agent may include bone growth promoting material, such as, for example, bone graft to enhance fixation of the components and/or surfaces of surgical system 100 with vertebrae. In some embodiments, the agent may include one or a plurality of therapeutic agents and/or pharmacological agents for release, including sustained release, to treat, for example, pain, inflammation and degeneration.

Figure 16:
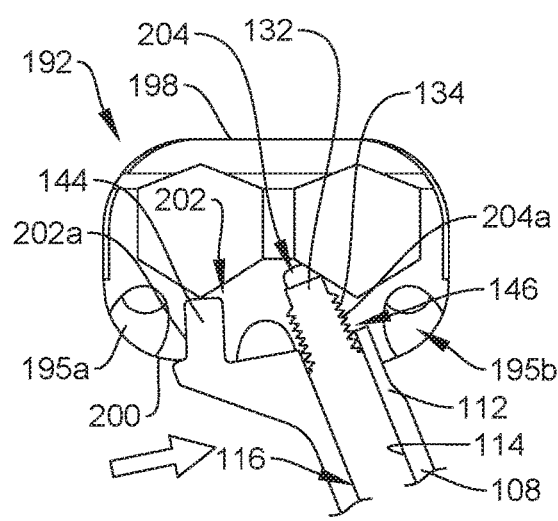
FIG. 16 is a side, breakaway, cross-sectional view of the second component shown in FIG. 14 coupled to the first component of the spinal system shown in FIG. 1.
Figure 17:
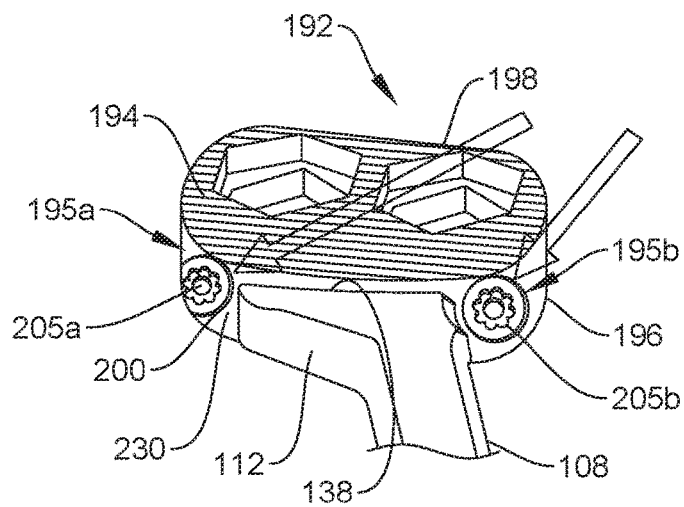
FIG. 17 is a perspective, breakaway view of the second component shown in FIG. 14 coupled to the first component of the spinal system shown in FIG. 1.
Figures 18, 19:
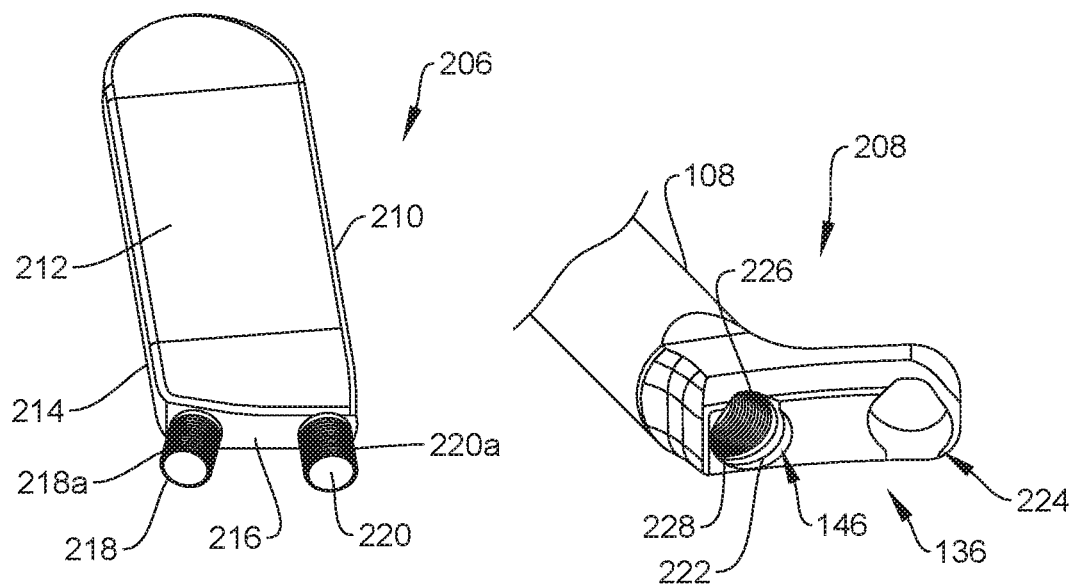
FIG. 18 is a perspective view of one embodiment of the second component of the spinal system shown in FIG. 1, in accordance with the principles of the present disclosure.
FIG. 19 perspective, breakaway view of one embodiment of the first component of the spinal system shown in FIG. 1, in accordance with the principles of the present disclosure.
Figures 20, 21:
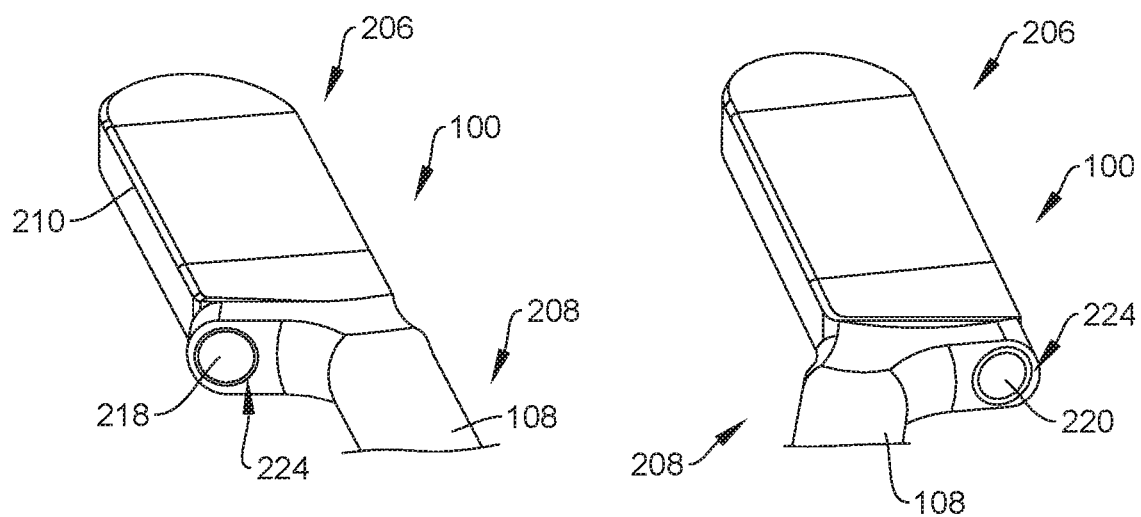
FIG. 20 is a perspective view of the first component shown in FIG. 19 coupled to the second component shown in FIG. 18.
FIG. 21 is a perspective view of the first component shown in FIG. 19 coupled to the second component shown in FIG. 18.

As shown above, instrument 104 was used to insert implant 192 in connection with an ALIF procedure. To demonstrate that instrument 104 can be used to insert implant 192 using different approaches, implant 192 is connected to instrument 104 by inserting peg 144 into cavity 202 such that opening 146 is aligned with cavity 204, as shown in FIG. 16 wherein implant 192 is configured for use in an OLIF 5-1 procedure. As shown in FIG. 17, implant 192 includes screw holes 195a, 195b that are accessible when peg 144 is inserted into cavity 202 and opening 146 is aligned with cavity 204 such that a fastener 205a can be inserted into and/or removed from hole 195a and a fastener 205b can be inserted into and/or removed from hole 195b when peg 144 is inserted into cavity 202 and opening 146 is aligned with cavity 204. Knob 130 in the first configuration when peg 144 is inserted into cavity 202 such that knob 130 is able to translate shaft 124 relative to sleeve 108 and handle 118 along axis X1 in the direction shown by arrow A in FIG. 1 and/or the direction shown by arrow B in FIG. 1. Knob 130 is translated relative to sleeve 108 and handle 118 along axis X1 in the direction shown by arrow A in FIG. 1 to move shaft 124 from a first position in which mating surface 134 is positioned entirely within passageway 116 to a second position in which mating surface 134 extends through opening 146 and into cavity 204, as shown in FIG. 16. Knob 130 is rotated about axis X1 in a first rotational direction, such as, for example, clockwise as knob 130 is translated relative to sleeve 108 and handle 118 along axis X1 in the direction shown by arrow A in FIG. 1 such that the male thread form of mating surface 134 mates with female thread form 204a. When the male thread form of mating surface 134 mates with female thread form 204a, further rotation of knob 130 relative to sleeve 108 and handle 118 in the first rotational direction causes shaft 124 to translate axially relative to sleeve 108 and handle 118 in the direction shown by arrow A in FIG. 1. Because knob 130 is in the first configuration, knob 130 is rotatable relative to sleeve 108 and handle 118 to translate shaft 124 axially relative to sleeve 108 and handle 118. As shaft 124 translates axially relative to sleeve 108 and handle 118 in the direction shown by arrow A in FIG. 1, knob 130 translates axially relative to plate 135 in the direction shown by arrow A in FIG. 1 to move knob 130 toward plate 135 such that extensions 160 are fully disposed in the openings 158 and knob 130 is in the second configuration.

Implant 192 is guided into intervertebral space IS using instrument 104. Once implant 192 is selectively positioned within intervertebral space IS knob 130 is rotated relative to sleeve 108 and handle 118 about axis X1 in a second rotational direction, such as, for example, counterclockwise. Knob 130 is rotated relative to sleeve 108 and handle 118 about axis X1 in the second rotational direction with a force sufficient to overcome the force of spring 182 to move knob 130 from the second configuration to the first configuration. As knob 130 moves from the second configuration to the first configuration, shaft 124 moves from the second position in which mating surface 134 extends through opening 146 and into cavity 202 to the first position in which mating surface 134 is positioned entirely within passageway 116. Peg 144 is removed from cavity 202 when shaft 124 is in the first position.

Figure 8:
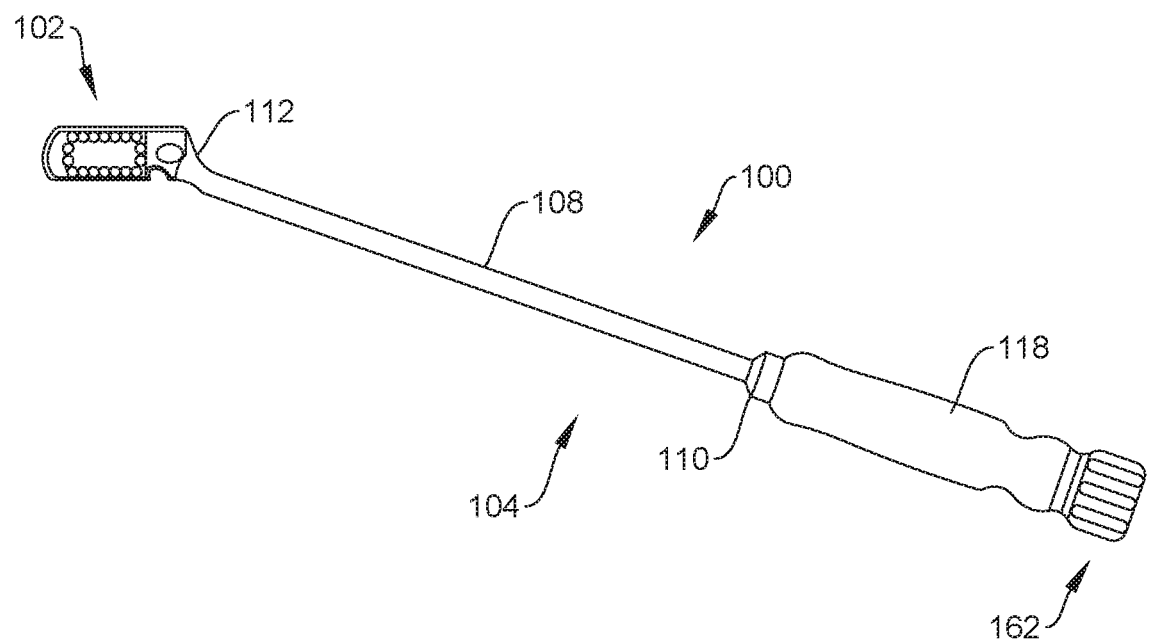
FIG. 8 is a side view of the first and second components of the spinal system shown in FIG. 1.
Figure 9:
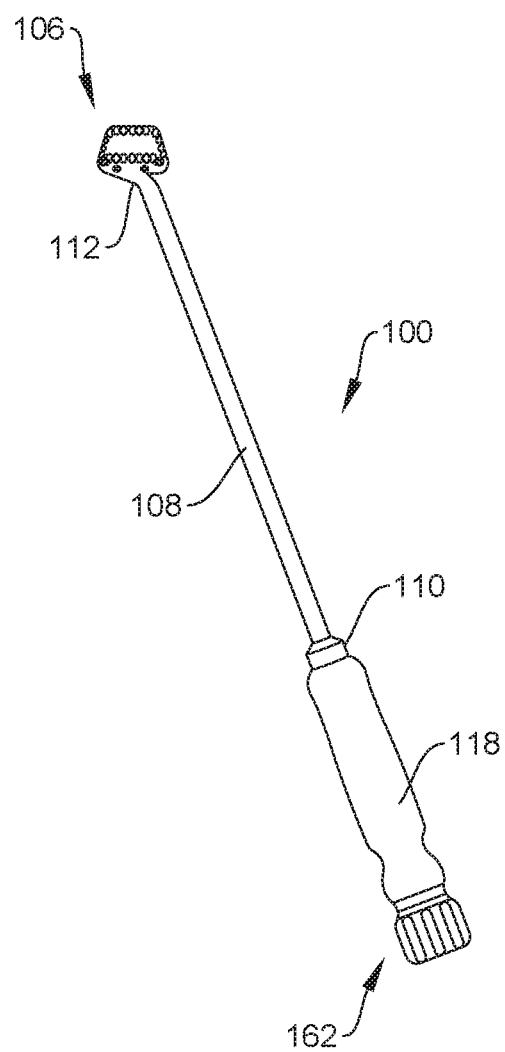
FIG. 9 is a side view of the first and second components of the spinal system shown in FIG. 2.
Figure 10:
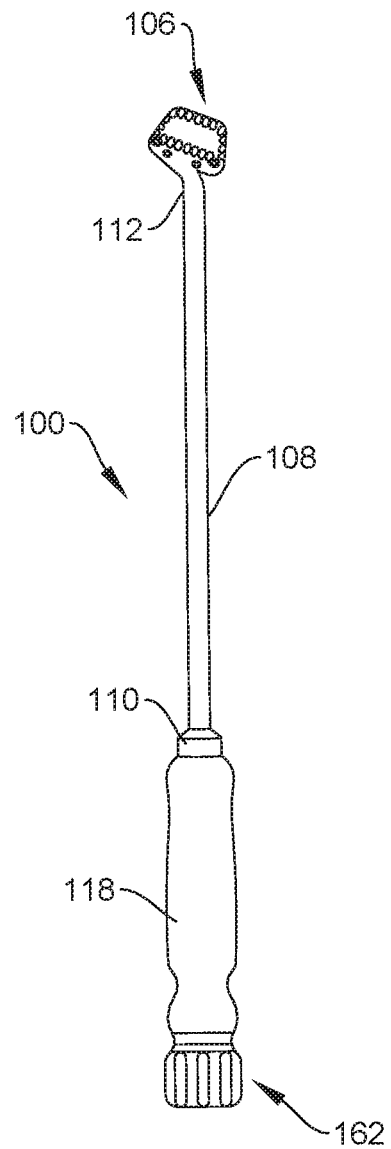
FIG. 10 is a side view of the first and second components of the spinal system shown in FIG. 2.

It should be appreciated that instrument 104 can be used to insert other implants, in addition to implant 192, for use in a variety of techniques, such as, for example, ALIF, OLIF 5-1, OLIF 2-5 and DLIF. For example, instrument 104 is shown in FIG. 1 connected to implant 102 to insert implant 102 in connection with an DLIF procedure. Instrument 104 is shown in FIG. 8 connected to implant 102 to insert implant 102 in connection with an OLIF 2-5 procedure. Instrument 104 is shown in FIG. 9 connected to implant 106 to insert implant 106 in connection with an OLIF 5-1 procedure. Instrument 104 is shown in FIG. 10 connected to implant 106 to insert implant 106 in connection with an ALIF procedure. However, it is envisioned that instrument 104 can be connected to a variety of implants that are the same or similar to implants 102, 106, 192 for use in a variety of different procedures and/or approaches.

In the embodiments discussed above, instrument 104 includes shaft 124 and peg 144 that are inserted into cavities of implants to connect instrument 104 to the implants. In other embodiments, implants are disclosed that include projections or extensions that are received within cavities of an instrument to couple the implant to the instrument. For example, in one embodiment, shown in FIGS. 18-21, surgical system 100 includes an implant 206 that is similar to implants 102, 106, 192 and an instrument 208 that is similar to instrument 104 and is configured to connect to implant 206 to insert implant 206 within a target area with a body of a patient, as discussed herein.

Figure 22:
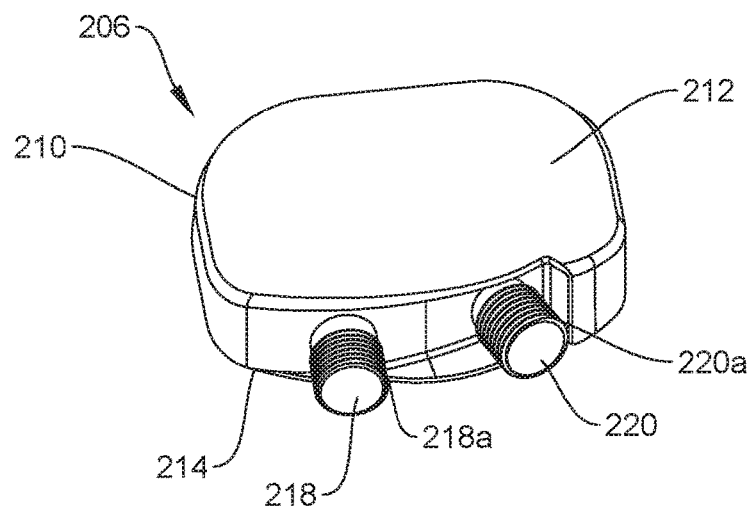
FIG. 22 is a perspective view of one embodiment of the second component of the spinal system shown in FIG. 1, in accordance with the principles of the present disclosure.
Figures 23, 24:
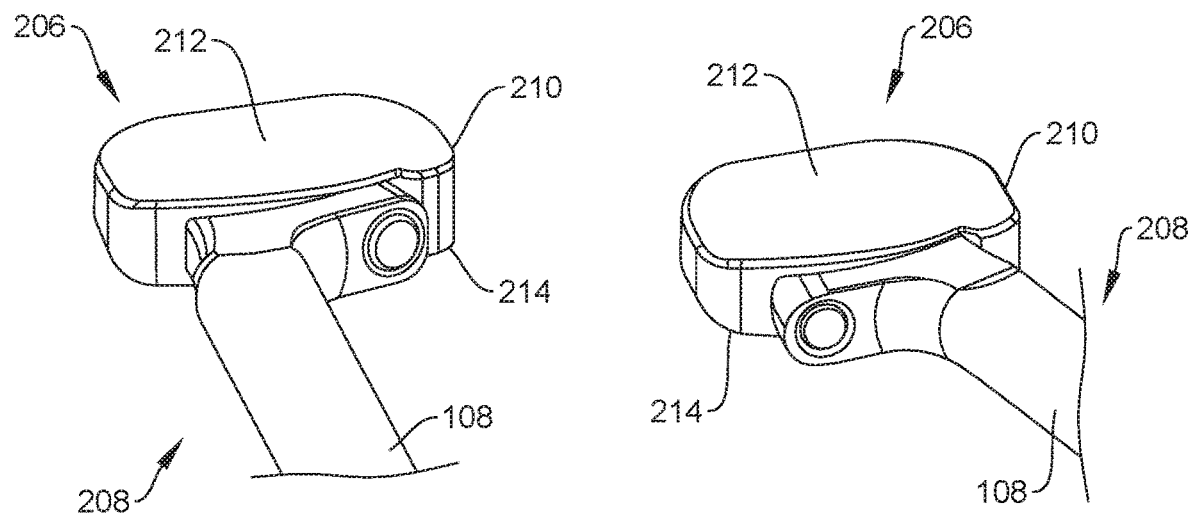
FIG. 23 is a perspective view of the first component shown in FIG. 19 coupled to the second component shown in FIG. 22.
FIG. 24 is a perspective view of the first component shown in FIG. 19 coupled to the second component shown in FIG. 22.

Implant 206 includes a body 210 having opposite first and second vertebral engaging surfaces 212, 214. As shown in FIGS. 22-24 body 210 of implant 206 can be provided with a variety of shapes and sizes. An end surface 216 of body 210 extends from vertebral engaging surface 212 to vertebral engaging surface 214. Implant 206 includes a peg 218 extending from surface 216 and a peg 220 extending from surface 216 such that peg 220 is spaced apart from peg 218. Peg 218 includes a male thread form 218a and peg 220 includes a male thread form 220a.

Instrument 208 includes sleeve 108. Rather than having shaft 124 positioned in passageway 116, instrument 208 includes an inner sleeve 222 rotatably positioned within 116 such that sleeve 222 can translate axially relative to axis X1 in opposite directions relative to sleeve 108. In one embodiment, an outer surface of sleeve 222 directly engages surface 114 when sleeve 222 is positioned in passageway 116. A proximal end of sleeve 222 is coupled to knob 130 to allow knob 130 to move sleeve 222 relative to sleeve 108 and handle 118 in the same manner as knob 130 moves shaft 124 relative to sleeve 108 and handle 118 in the embodiments of instrument 104 discussed above. Engagement portion 136 of instrument 208 is similar to engagement portion 136 of instrument 104 except that engagement portion 136 of instrument 208 includes an aperture 224 in place of peg 144. Sleeve 222 includes an inner surface 226 that defines a female thread form 228 configured to engage male thread form 218a or male thread form 220a to couple implant 206 to instrument 208, as discussed herein.

In assembly, operation and use, instrument 208 is coupled to an implant, such as, for example, implant 206, that is configured to be inserted into a target site, such as, for example, intervertebral space IS. In one embodiment, implant 206 is configured for use in an ALIF procedure. Implant 206 is connected to instrument 208 by inserting peg 218 into aperture 224 such that opening 146 is aligned with peg 220. Knob 130 in the first configuration when peg 218 is inserted into aperture 224 such that knob 130 is able to translate sleeve 222 relative to sleeve 108 and handle 118 along axis X1 in the direction shown by arrow A in FIG. 1 and/or the direction shown by arrow B in FIG. 1. Knob 130 is translated relative to sleeve 108 and handle 118 along axis X1 in the direction shown by arrow A in FIG. 1 to move sleeve 222 from a first position in which sleeve 222 is positioned entirely within passageway 116 to a second position in which sleeve 222 extends through opening 146 and engages peg 220.

Knob 130 is rotated about axis X1 in a first rotational direction, such as, for example, clockwise as knob 130 is translated relative to sleeve 108 and handle 118 along axis X1 in the direction shown by arrow A in FIG. 1 such that the female thread form 228 mates with male thread form 220a. When female thread form 228 mates with male thread form 220a, further rotation of knob 130 relative to sleeve 108 and handle 118 in the first rotational direction causes sleeve 222 to translate axially relative to sleeve 108 and handle 118 in the direction shown by arrow A in FIG. 1. Because knob 130 is in the first configuration, knob 130 is rotatable relative to sleeve 108 and handle 118 to translate sleeve 222 axially relative to sleeve 108 and handle 118. As sleeve 222 translates axially relative to sleeve 108 and handle 118 in the direction shown by arrow A in FIG. 1, knob 130 translates axially relative to plate 135 in the direction shown by arrow A in FIG. 1 to move knob 130 toward plate 135 such that extensions 160 are fully disposed in the openings 158 and knob 130 is in the second configuration.

Implant 206 is guided into intervertebral space IS using instrument 208. Once implant 206 is selectively positioned within intervertebral space IS knob 130 is rotated relative to sleeve 108 and handle 118 about axis X1 in a second rotational direction, such as, for example, counterclockwise. Knob 130 is rotated relative to sleeve 108 and handle 118 about axis X1 in the second rotational direction with a force sufficient to overcome the force of spring 182 to move knob 130 from the second configuration to the first configuration. As knob 130 moves from the second configuration to the first configuration, sleeve 222 moves from the second position in which sleeve 222 extends through opening 146 and engages peg 220 to the first position in which sleeve 222 is positioned entirely within passageway 116.

As shown above, instrument 208 was used to insert implant 206 in connection with an ALIF procedure. To demonstrate that instrument 208 can be used to insert implant 206 using different approaches, implant 206 is connected to instrument 208 by inserting peg 220 into aperture 224 such that opening 146 is aligned with peg 218. Knob 130 in the first configuration when peg 220 is inserted into aperture 224 such that knob 130 is able to translate sleeve 222 relative to sleeve 108 and handle 118 along axis X1 in the direction shown by arrow A in FIG. 1 and/or the direction shown by arrow B in FIG. 1. Knob 130 is translated relative to sleeve 108 and handle 118 along axis X1 in the direction shown by arrow A in FIG. 1 to move sleeve 222 from a first position in which sleeve 222 is positioned entirely within passageway 116 to a second position in which sleeve 22 extends through opening 146 and engages peg 218. Knob 130 is rotated about axis X1 in a first rotational direction, such as, for example, clockwise as knob 130 is translated relative to sleeve 108 and handle 118 along axis X1 in the direction shown by arrow A in FIG. 1 such that female thread form 228 mates with male thread form 218a. When the female thread form 228 mates with male thread form 218a, further rotation of knob 130 relative to sleeve 108 and handle 118 in the first rotational direction causes sleeve 222 to translate axially relative to sleeve 108 and handle 118 in the direction shown by arrow A in FIG. 1. Because knob 130 is in the first configuration, knob 130 is rotatable relative to sleeve 108 and handle 118 to translate sleeve 222 axially relative to sleeve 108 and handle 118. As sleeve 222 translates axially relative to sleeve 108 and handle 118 in the direction shown by arrow A in FIG. 1, knob 130 translates axially relative to plate 135 in the direction shown by arrow A in FIG. 1 to move knob 130 toward plate 135 such that extensions 160 are fully disposed in the openings 158 and knob 130 is in the second configuration.

Implant 206 is guided into intervertebral space IS using instrument 208. Once implant 206 is selectively positioned within intervertebral space IS knob 130 is rotated relative to sleeve 108 and handle 118 about axis X1 in a second rotational direction, such as, for example, counterclockwise. Knob 130 is rotated relative to sleeve 108 and handle 118 about axis X1 in the second rotational direction with a force sufficient to overcome the force of spring 182 to move knob 130 from the second configuration to the first configuration. As knob 130 moves from the second configuration to the first configuration, shaft 124 moves from the second position in which sleeve 222 extends through opening 146 to the first position in which sleeve 222 is positioned entirely within passageway 116. It should be appreciated that instrument 208 can be used to insert other implants, in addition to implant 206, for use in a variety of techniques, such as, for example, ALIF, OLIF 5-1, OLIF 2-5 and DLIF.

Figure 12:
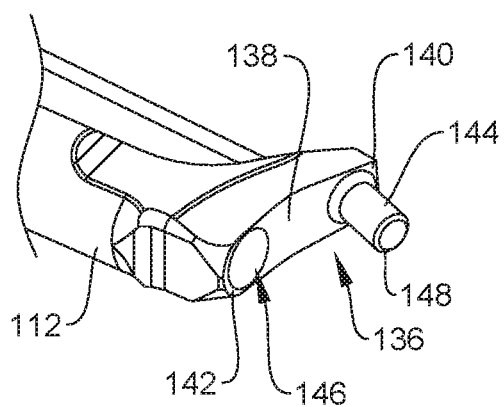
FIG. 12 is a perspective, breakaway view of the distal end of one embodiment of the first component of the spinal system shown in FIG. 1, in accordance with the principles of the present disclosure.
Figure 13:
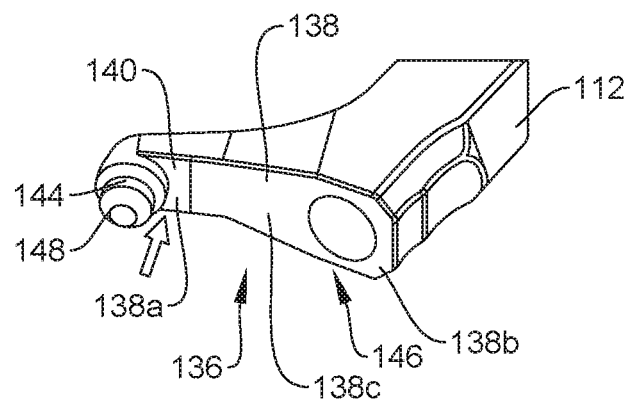
FIG. 13 is a perspective, breakaway view of one embodiment of the distal end of the first component of the spinal system shown in FIG. 1, in accordance with the principles of the present disclosure.
Figure 14:
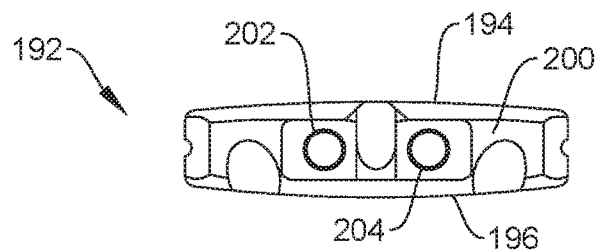
FIG. 14 is a side view of one embodiment of the second component of the spinal system shown in FIG. 1, in accordance with the principles of the present disclosure.
Figure 25:
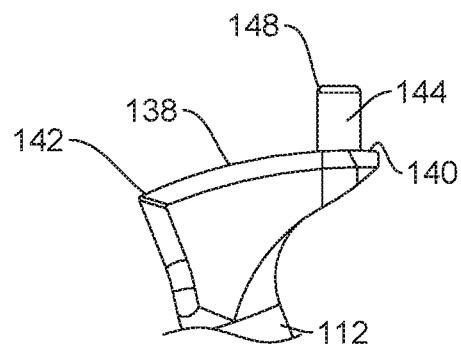
FIG. 25 is a perspective, breakaway view of one embodiment of the first component of the spinal system shown in FIG. 1, in accordance with the principles of the present disclosure.
Figure 26:
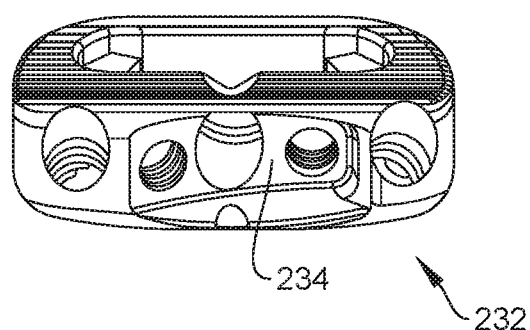
FIG. 26 is a perspective view of one embodiment of the second component of the spinal system shown in FIG. 1, in accordance with the principles of the present disclosure.
Figure 27:
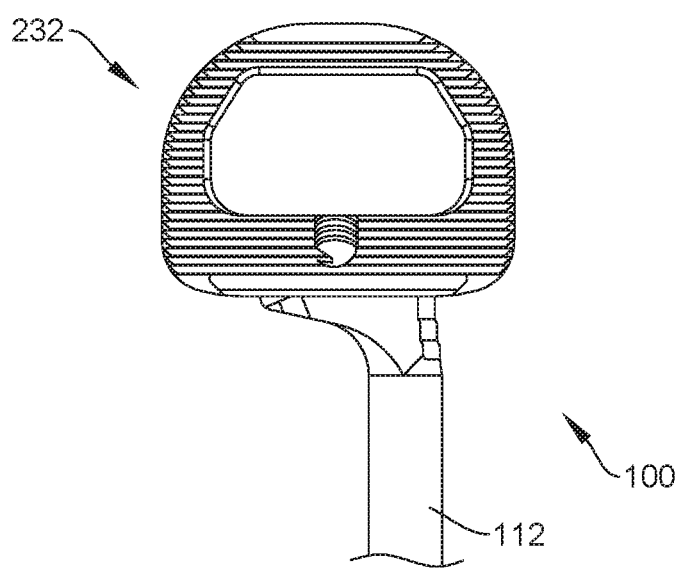
FIG. 27 is a top, breakaway view of the first component shown in FIG. 25 coupled to the second component shown in FIG. 26.

As discussed above, engagement portion 136 can be variously configured for engagement with a plurality of different implants. That is, the configuration of engagement portion 136 can be adapted to match the configuration of an implant. For example, in one embodiment, shown in FIG. 12, engagement surface 138 is concavely curved from end 140 to end 142. In some embodiments, engagement surface 138 is continuously curved from end 140 to end 142 and/or engagement surface 138 has a continuous radius of curvature. The configuration of engagement surface 138 in FIG. 11 could be used in connection with implants that include a convexly curved surface that engages engagement surface 138, such as, for example, engagement surface 230 of implant 192. In another embodiment, shown in FIG. 13, engagement surface 138 includes a first planar portion 138a, a second planar portion 138b and a third planar portion 138c between portion 138a and portion 138b. Peg 144 extends from portion 138a and opening 146 extends through portion 138b. Portion 138c extends at an acute angle relative to portion 138a and portion 138c. In one embodiment, shown in FIG. 25, engagement surface 138 is convexly curved from end 140 to end 142. In some embodiments, engagement surface 138 is continuously curved from end 140 to end 142 and/or engagement surface 138 has a continuous radius of curvature. The configuration of engagement surface 138 in FIG. 25 could be used in connection with an implant 232 that include a concavely curved surface 234, FIG. 26, configured for engagement with engagement surface 138, as shown in FIG. 27.

Figure 28:
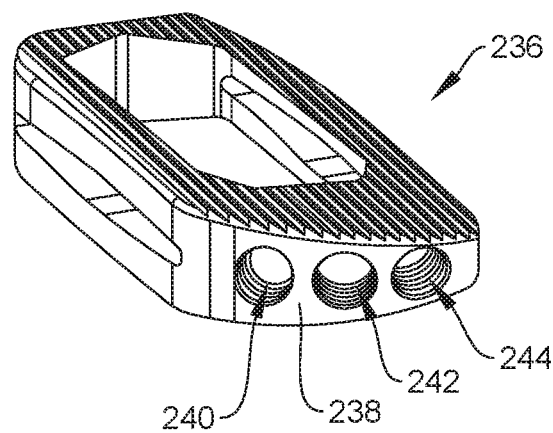
FIG. 28 is a perspective view of one embodiment of the second component of the spinal system shown in FIG. 1, in accordance with the principles of the present disclosure.
Figures 29, 30, 31, 32:
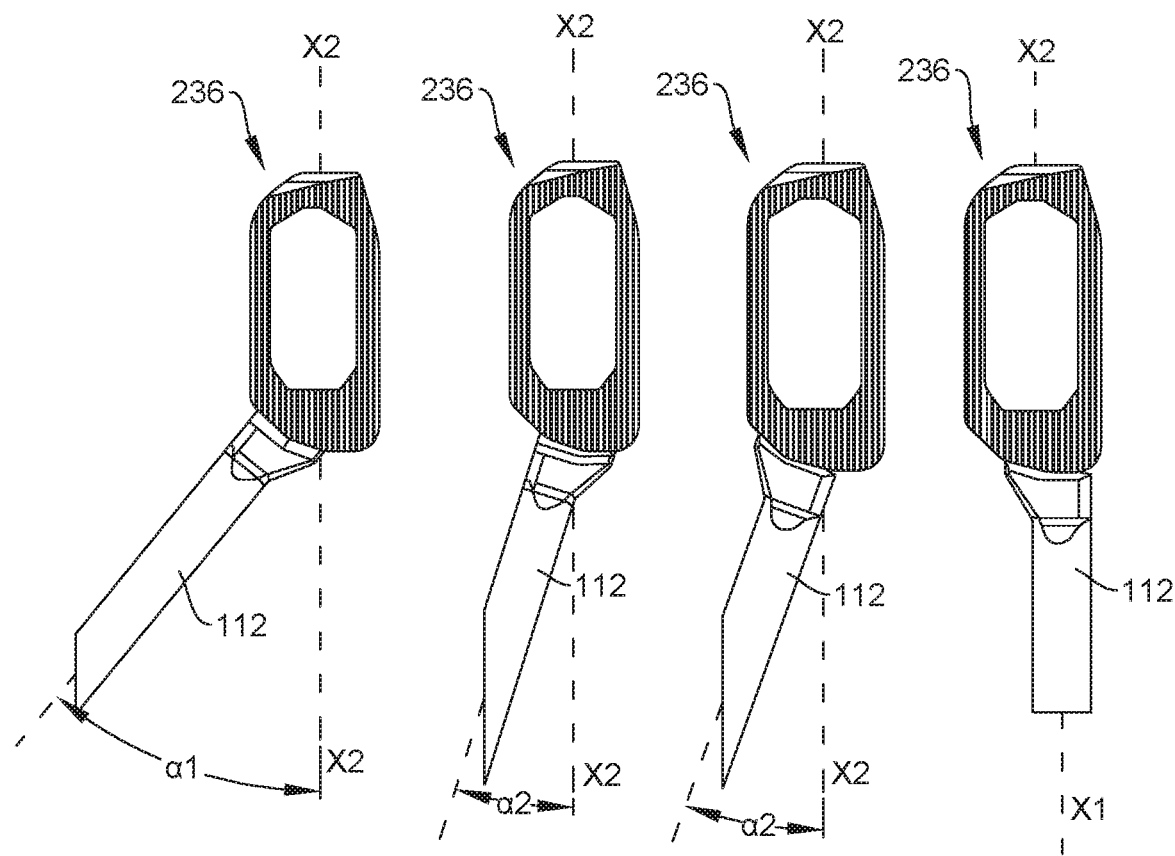
FIG. 29 is a top, breakaway view of the second component shown in FIG. 28 coupled to the first component of the spinal system shown in FIG. 1.
FIG. 30 is a top, breakaway view of the second component shown in FIG. 28 coupled to the first component of the spinal system shown in FIG. 1.
FIG. 31 is a top, breakaway view of the second component shown in FIG. 28 coupled to the first component of the spinal system shown in FIG. 1.
FIG. 32 is a top, breakaway view of the second component shown in FIG. 28 coupled to the first component of the spinal system shown in FIG. 1.

The implants discussed above each include two threaded cavities along an engagement surface (e.g., cavities 202, 204 along surface 200) for disposal of peg 144 and shaft 124, respectively. However, it is envisioned that the implants discussed herein may include three or more threaded cavities along an engagement surface. In some embodiments, the threaded cavities are all on an arc path defined by the engagement surface. For example, cavities 202, 204 of implant 192 are on an arc path of surface 200 and coincide with an arc center of surface 200. It is envisioned that providing an implant with at least three cavities will allow a medical practitioner greater options for connecting an implant to instrument 104. For example, the three of more cavities allow instrument 104 to be attached to the implant at different angles or at the same angle in different ways. In one embodiment, shown in FIG. 28, an implant 238 includes an anterior surface 238 that includes spaced apart threaded cavities 240, 242, 244 along an arc path of surface 238. In one embodiment, shown in FIG. 29, peg 144 is disposed in cavity 242 and end 132 of shaft 124 is disposed in cavity 240 such that an axis X2 of implant 236 is disposed at an angle α1 relative to axis X1. In one embodiment, shown in FIG. 30, peg 144 is disposed in cavity 244 and end 132 of shaft 124 is disposed in cavity 242 such that axis X2 of implant 236 is disposed at an angle α2 relative to axis X1. In one embodiment, shown in FIG. 31, peg 144 is disposed in cavity 240 and end 132 of shaft 124 is disposed in cavity 242 such that axis X2 of implant 236 is disposed at angle α2 relative to axis X1. In one embodiment, shown in FIG. 32, peg 144 is disposed in cavity 242 and end 132 of shaft 124 is disposed in cavity 244 such that axis X2 parallel and/or coaxial with axis X1. In some embodiments, angle α1 is about 40 degrees and angle α2 is about 20 degrees.

Figure 33:
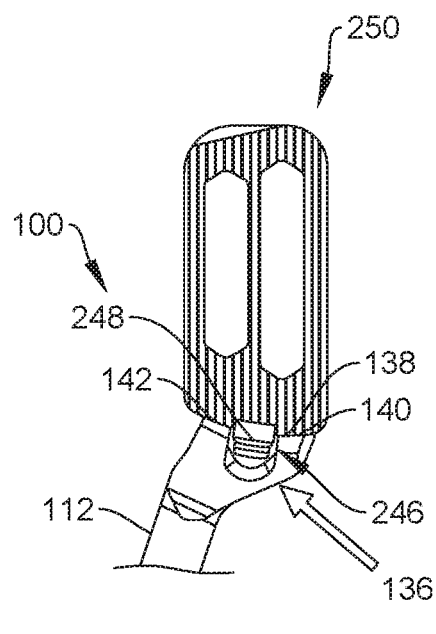
FIG. 33 is a top, breakaway view of one embodiment of the first component of the spinal system shown in FIG. 1 coupled to one embodiment of the second component of the spinal system shown in FIG. 1, in accordance with the principles of the present disclosure.
Figure 34:
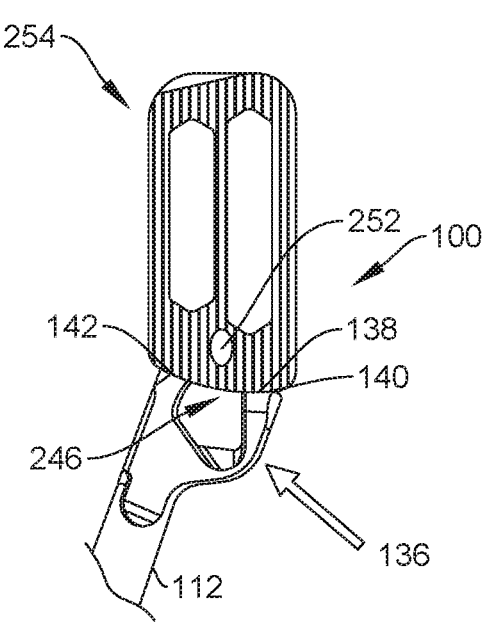
FIG. 34 is a top, breakaway view of one embodiment of the first component of the spinal system shown in FIG. 1 coupled to one embodiment of the second component of the spinal system shown in FIG. 1, in accordance with the principles of the present disclosure.
Figure 35:
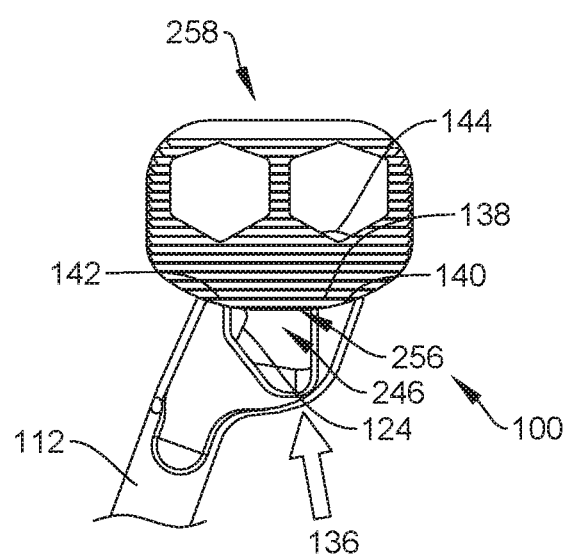
FIG. 35 is a top, breakaway view of one embodiment of the component of the spinal system shown in FIG. 1 coupled to one embodiment of the second component of the spinal system shown in FIG. 1, in accordance with the principles of the present disclosure.

In some embodiments, shown in FIGS. 33-35, engagement surface 138 includes a gap 246 between end 140 and end 142. That is, end 142 is spaced apart from end 140 by gap 246. In one embodiment, shown in FIG. 33, gap 246 is configured for disposal of a plate 248 that is coupled to an implant 250 to allow implant 250 to be inserted with instrument 104 while plate 248 is attached to implant 250. That is, plate 248 can be coupled to implant 250 before instrument 104 engages implant 250 to deliver implant 250 to a target site. In one embodiment, shown in FIG. 34, gap 246 is configured to allow access to a screw hole 252 of an implant 254 while instrument 104 is attached to implant 254. That is, a fastener can be inserted through hole 252 and into tissue, such as, for example, bone while instrument 104 is attached to implant 254, to secure implant 254 relative to tissue. Once the fastener is inserted through hole 252 and into tissue, instrument 104 can be removed from implant 254. Likewise, in one embodiment, shown in FIG. 35, gap 246 is configured to allow access to a screw hole 256 of an implant 258 while instrument 104 is attached to implant 258. That is, a fastener can be inserted through hole 256 and into tissue, such as, for example, bone while instrument 104 is attached to implant 258, to secure implant 258 relative to tissue. Once the fastener is inserted through hole 256 and into tissue, instrument 104 can be removed from implant 258.

As discussed herein, instrument 104 can be used for insertion of a plurality of different implants. In one embodiment, shown in FIGS. 36-41, system 100 includes an implant 260 having a solid body 262 extending along a longitudinal axis X3 between an end wall 264 and an opposite end wall 266. Body 262 includes a side wall 268 and a side wall 270 opposite side wall 268. Walls 268, 270 each extend from wall 264 to wall 266. In some embodiments, at least one of walls 268, 270 is planar from wall 264 to wall 270. In some embodiments, at least one of walls 268, 270 extends parallel to axis X3. In some embodiments, at least one of walls 264, 266 is convexly curved from wall 268 to wall 270. In some embodiments, at least one of walls 264, 266 has a continuous radius of curvature from wall 268 to wall 270. However, it is envisioned that walls 264, 266 can be variously shaped and/or curved to match the shape and/or curve of an engagement surface of an instrument that engages one of walls 264, 266, such as, for example, engagement surface 138 of instrument 104. In some embodiments, walls 264, 266 each have a maximum length that is less than maximum lengths of walls 268, 270. In some embodiments, wall 264 extends perpendicular to wall 268, wall 268 extends perpendicular to wall 266, wall 266 extends perpendicular to wall 270 and wall 270 extends perpendicular to wall 264.

Inner surfaces of walls 264, 266, 268, 270 define a cavity 272. In some embodiments, body 262 includes a scaffold 274 positioned within cavity 272. Scaffold 274 includes a top wall 276 and an opposite bottom wall 278. Wall 278 is connected to wall 276 by a plurality of spaced apart ribs 280. Scaffold 274 is connected to wall 268 by a support 282 and is connected to wall 270 by a support 284. Scaffold 274 is spaced apart from wall 264 and wall 266 and is only connected to walls 268, 270 by supports 282, 284. Scaffold 274 includes an opening 286 that extends through wall 276 and an opening 288 that extends through wall 278. Openings 286, 288 extend perpendicular to axis X3. Scaffold 274 includes a plurality of apertures 290 extending through a thickness of wall 276 and a plurality of apertures 292 extending through a thickness of wall 278. In some embodiments, body 262 includes a window 294 that extends through wall 268 and a window 296 that extends through wall 270. In some embodiments, apertures 290, apertures 292, window 294 and/or window 296 may be variously shaped, such as, for example, oval, oblong, triangular, square, polygonal, irregular, uniform, non-uniform, offset, staggered, undulating, arcuate, variable and/or tapered. In some embodiments, wall 268 and/or wall 270 may be disposed at alternate orientations, relative to axis X3, such as, for example, transverse, perpendicular and/or other angular orientations such as acute or obtuse, co-axial and/or may be offset or staggered. In some embodiments, apertures 290 and/or apertures 292 may be variously shaped, such as, for example, circular, oval, oblong, triangular, square, hexagonal, polygonal, honeycomb-shaped, irregular, uniform, non-uniform, offset, staggered, undulating, arcuate, variable and/or tapered.

Figure 39:
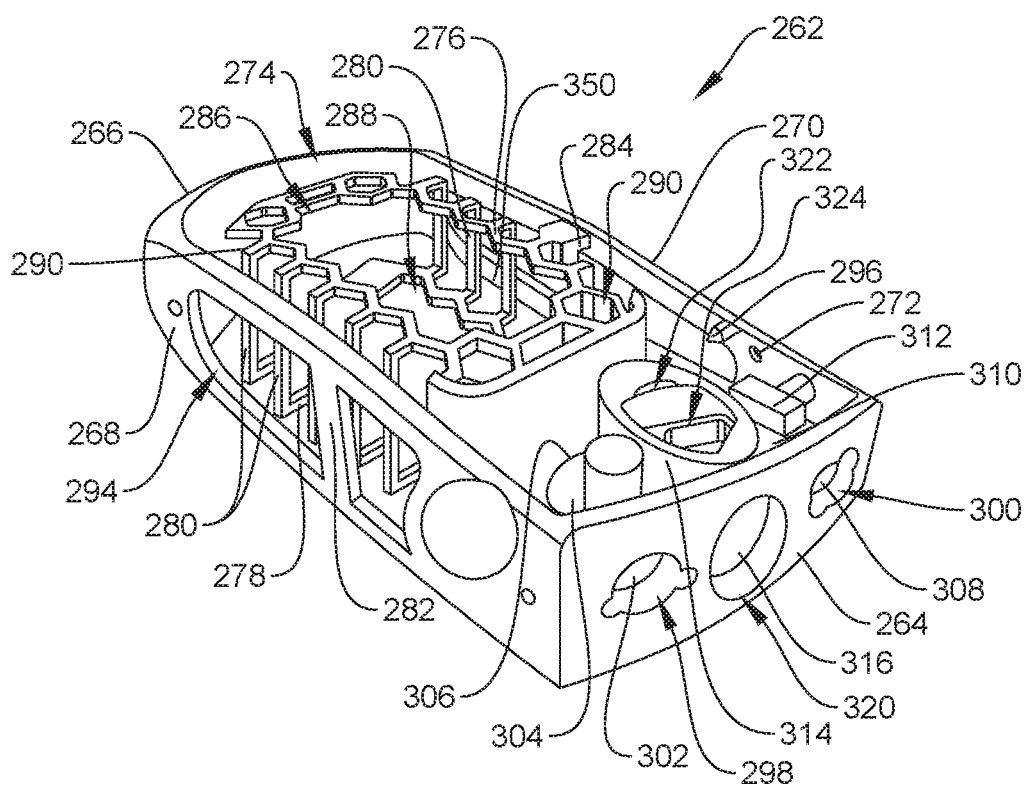
FIG. 39 is a perspective view of the second component shown in FIG. 36, with parts separated.

Body 262 includes a cavity 298 and a cavity 300 that is spaced apart from cavity 298. Cavities 298, 300 each extend into wall 264. In some embodiments, cavity 298 is in communication with a passageway 302 defined by a cylindrical wall 304 of body 262 that is coupled to wall 264, as best shown in FIG. 39. Wall 304 includes a closed end 306 such that cavity 298 and passageway 302 are not in communication with cavity 272. That is, an object must be inserted through wall 264 to be inserted into cavity 298 and passageway 302. Likewise, cavity 300 is in communication with a passageway 308 defined by a cylindrical wall 310 of body 262 that is coupled to wall 264, as best shown in FIG. 39. Wall 310 includes a closed end 312 such that cavity 300 and passageway 308 are not in communication with cavity 272. That is, an object must be inserted through wall 264 to be inserted into cavity 300 and passageway 308. Cavities 298, 300 and passageways 302, 308 are configured for engagement with components of an instrument, such as, for example, peg 144 and shaft 124 of instrument 104, as discussed herein. As such, passageways 302, 308 each include a female thread form configured to mate with the male thread form of mating surface 134 to connect instrument with implant 260, as discussed herein. Walls 304, 310 are permanently fixed relative to body 262. That is, walls 304, 310 are incapable of moving relative to walls 264, 266, 268, 270 such that wall 304 does not move when peg 144 is positioned in passageway 308 to allow mating surface 134 to engage the female thread form of passageway 302 and/or wall 310 does not move when peg 144 is positioned in passageway 302 to allow mating surface to engage the female thread form of passageway 308. Indeed, having walls 304, 310 permanently fixed relative to body 262 allows instrument 104 to be manipulated relative to implant 260 to couple implant 260 to instrument 104, as discussed herein. In contrast to systems that include instruments that are configured to move an implant relative to the instrument when the implant is coupled to the instrument, implant 260 will be fixed to instrument 104 when instrument 104 is connected to implant 260. As such, a medical practitioner must manually manipulate handle 118 while implant 260 is fixed to instrument 104 to selectively position implant 260 within a patient. In some embodiments, cavity 298, cavity 300, passageway 302, passageway 308, opening 320, opening 322 and/or passageway 324 may be disposed at alternate orientations, relative to axis X3, such as, for example, transverse, perpendicular and/or other angular orientations such as acute or obtuse, co-axial and/or may be offset or staggered.

In some embodiments, body 262 includes a tunnel 314 having an end 316 that is fixed to wall 264 and an opposite end 318. Tunnel 314 extends at an oblique angle relative to axis X3 and is positioned between cavity 298 and cavity 300 and includes an opening 320 that extends through end 316 and wall 264 and an opening 322 that extends through end 318. Tunnel 314 extends continuously from opening 320 to opening 322 such that tunnel 314 is free of any gaps or openings between opening 320 and opening 322 and a bore, such as, for example, a passageway 324 defined by an inner surface of tunnel 314 is not in communication with cavity 272, cavity 298, cavity 300, passageway 304 or passageway 308. Passageway 324 is configured for disposal of a fastener, such as, for example, a bone screw such that the bone screw extends through openings 320, 322 for engagement with tissue, such as, for example, bone, as discussed herein. It is envisioned that body 262 can include one ore more tunnels in addition to tunnel 314 wherein the additional tunnels are each configured for disposal of an additional bone screw such that implant 260 can be attached to bone using more than one bone screw. In some embodiments, tunnel 314 may be disposed at alternate orientations, relative to axis X3, such as, for example, parallel, transverse, perpendicular and/or other angular orientations such as acute or obtuse, co-axial and/or may be offset or staggered.

A core 326 is positioned in cavity 272 such that core 326 surrounds scaffold 274 and is viewable through windows 294, 296. Core 326 includes a body 328 having a lattice configuration that reduces stiffness and opacity, while maintaining strength. Body 328 extends from an inner surface of wall 264 to scaffold 274, from an inner surface of wall 266 to scaffold 274, from an inner surface of wall 268 to scaffold 274 and from an inner surface of wall 270 to scaffold 274. In some embodiments, an uppermost surface of body 328 is flush with an uppermost surface of body 262 and a lowermost surface of body 328 is flush with a lowermost surface of body 262 when core 326 is positioned within cavity 272. Core 326 extends a central channel 330 that extends through a thickness of body 328 defined by the distance between the uppermost and lowermost surfaces of body 328. Channel 330 is aligned with openings 286, 288 when core 326 is positioned within cavity 272. In some embodiments, core 326 is fused with body 262. In some embodiments, core 326 is welded to body 262. In some embodiments, core 326 is integrally and/or monolithically formed with body 262.

Figures 40, 40A:
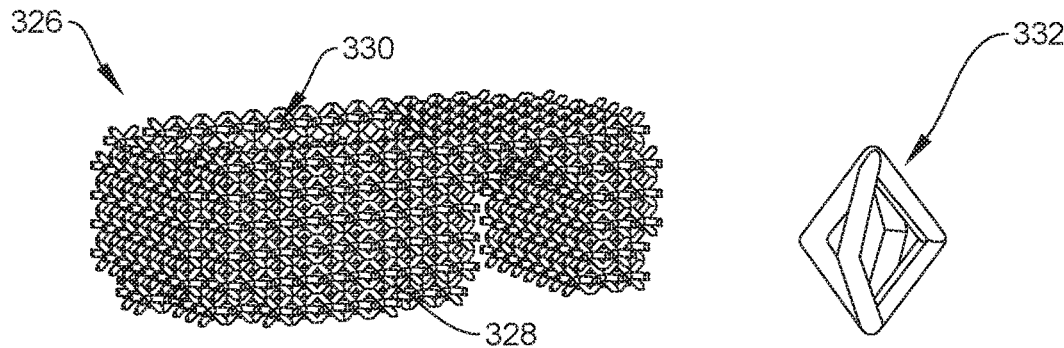
FIG. 40 is a perspective view of the second component shown in FIG. 36, with parts separated.
FIG. 40A is a detailed view of a portion of the second component shown in FIG. 36.
Figures 40B, 40C:
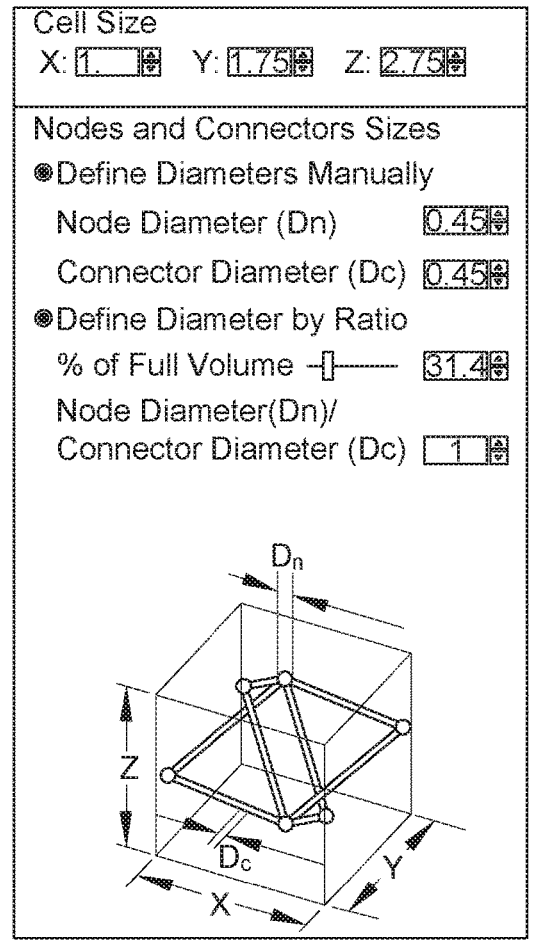
FIG. 40B is a chart showing structural characteristics of a portion of the second component shown in FIG. 36.
FIG. 40C is a user interface showing structural characteristics of a portion of the second component shown in FIG. 36.
Figure 41:
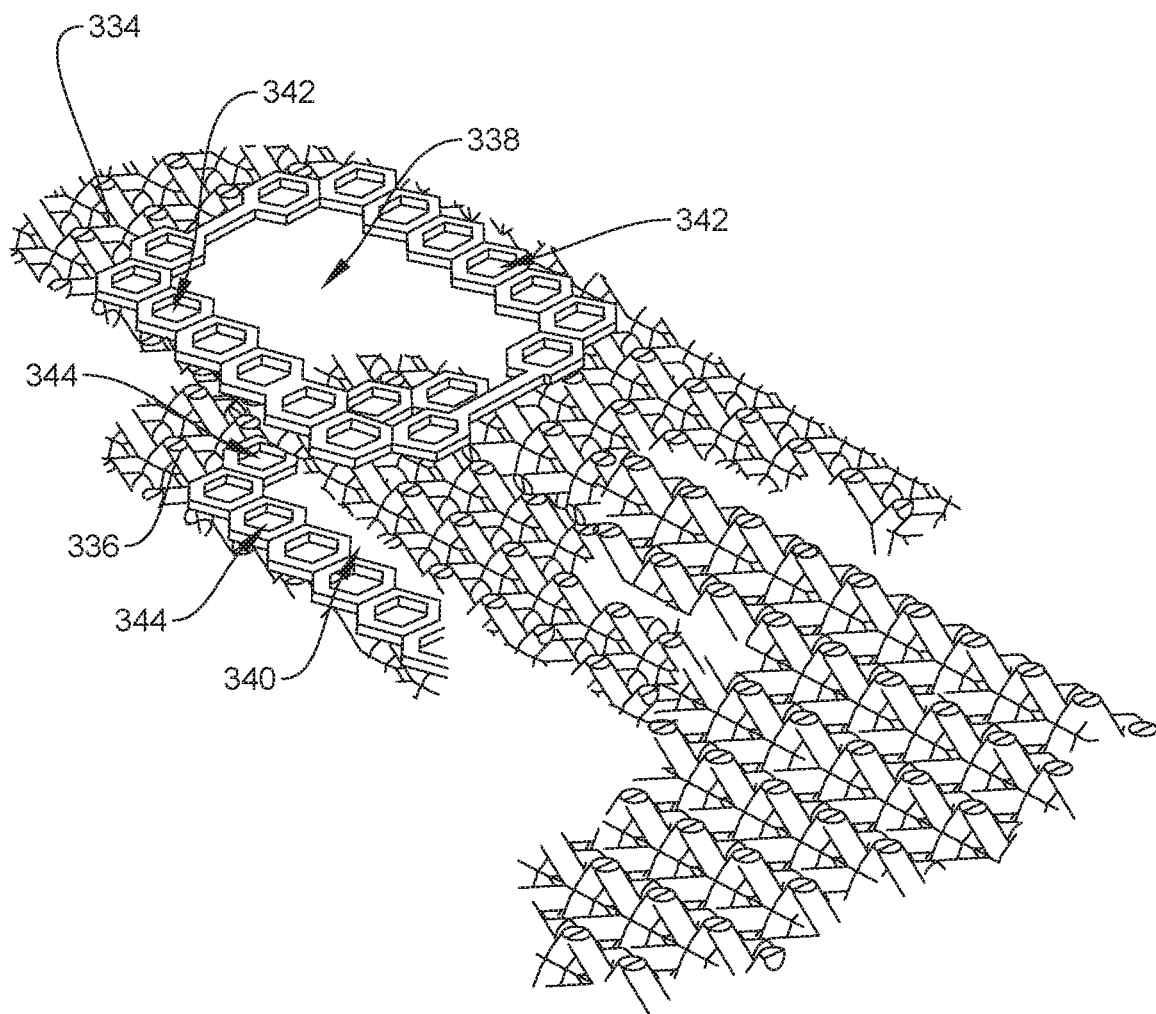
FIG. 41 is a perspective view of the second component shown in FIG. 36, with parts separated.
Figure 48:
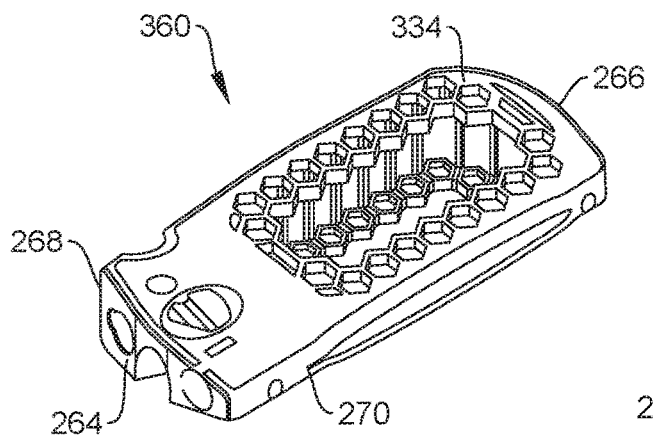
FIG. 48 is a perspective view of one embodiment of the second component of the spinal system shown in FIG. 1, in accordance with the principles of the present disclosure.

In some embodiments, the lattice configuration of body 328 is a diamond lattice the provides exceptional buildability, strength, reduced internal stress and fits within a variety of spinal implant type geometries. That is, the lattice configuration of body 328 is formed from a plurality of diamonds 332 that are coupled together to form body 328. The parameters of diamonds 332 are shown in FIG. 40B. However, it is envisioned that the parameters of diamonds 332 can be altered by changing x, y and z values of diamonds 332 in a user interface, as shown in FIG. 40C. In some embodiments, the lattice configuration of body 328 is formed using 3D printing.

Implant 26 includes a cap 334 coupled to top ends of walls 264, 266, 268, 270 and scaffold 274 and a cap 336 coupled to opposite bottom ends of walls 264, 266, 268, 270 and scaffold 274. Cap 334 includes an opening 338 that is aligned with opening 286 and channel 330 when cap 334 is coupled to bodies 262, 328 and cap 336 includes an opening 340 that is aligned with opening 288 and channel when cap 336 is coupled to bodies 262, 328. Opening 338 is surrounded by a plurality of apertures 342 and opening 340 is surrounded by a plurality of apertures 344. Apertures 342 are aligned with apertures 290 when cap 334 is coupled to bodies 262, 328 and apertures 344 are aligned with apertures 292 when cap 336 is coupled to bodies 262, 328. In some embodiments, apertures 342 have the same size and shape as apertures 290 and/or apertures 344 have the same size and shape as apertures 292. In some embodiments, caps 334, 336 are fused with body 262 and/or body 328. In some embodiments, caps 334, 336 are welded to body 262 and/or body 328. In some embodiments, caps 334, 336 are integrally and/or monolithically formed with body 262 and/or body 328.

Figure 36:
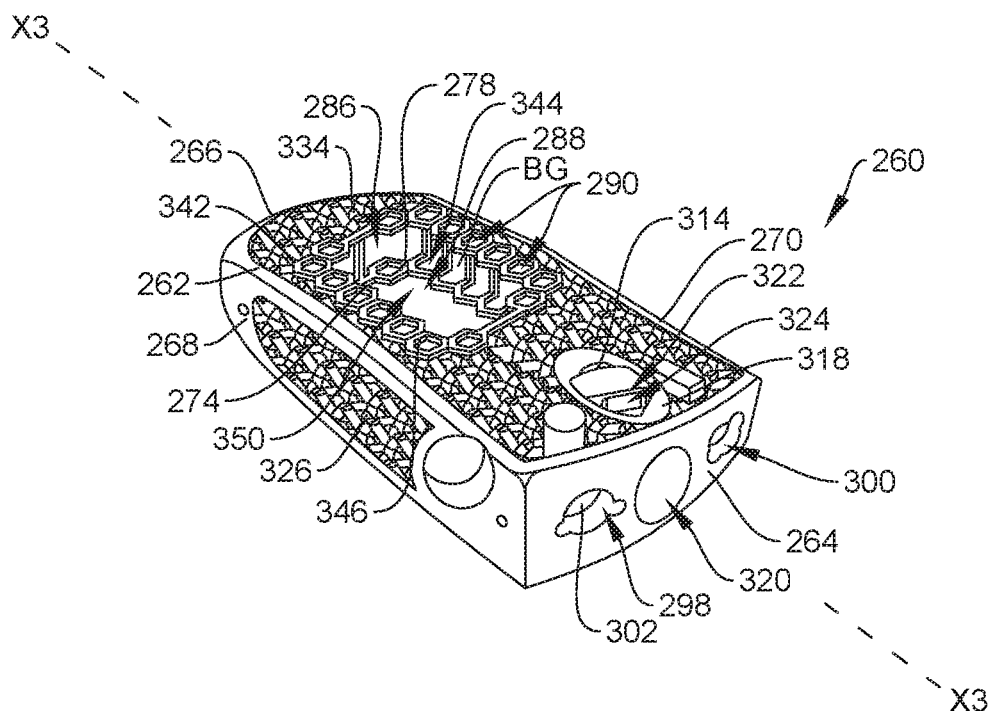
FIG. 36 is a perspective view of one embodiment of the second component of the spinal system shown in FIG. 1, in accordance with the principles of the present disclosure.
Figure 37:
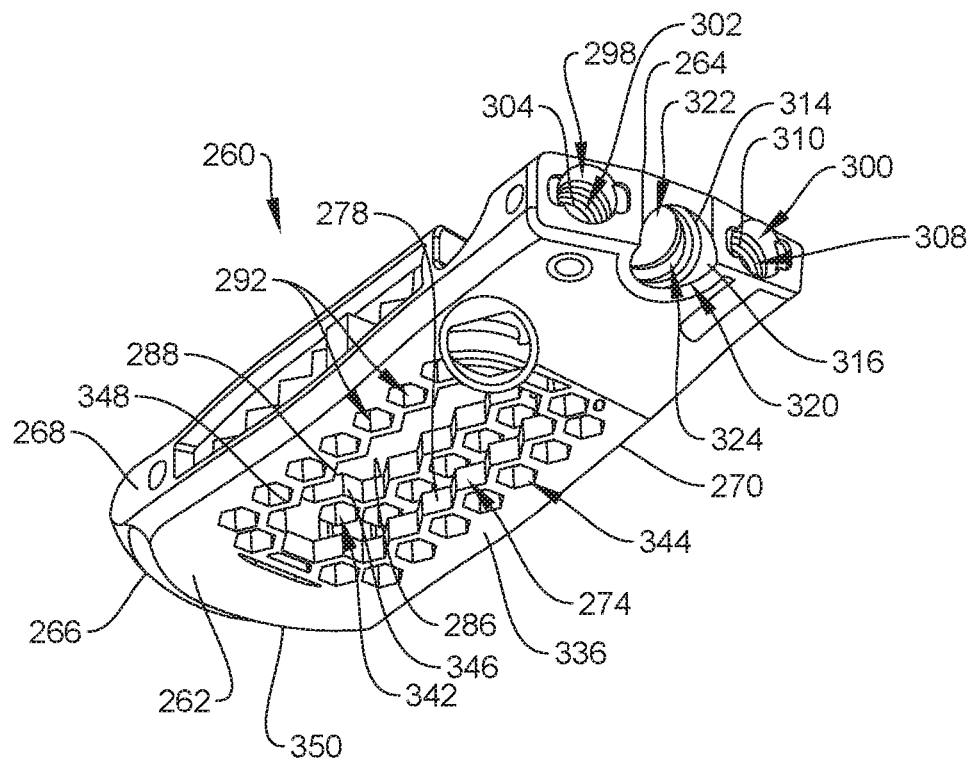
FIG. 37 is a perspective view of the second component shown in FIG. 36.
Figure 38:
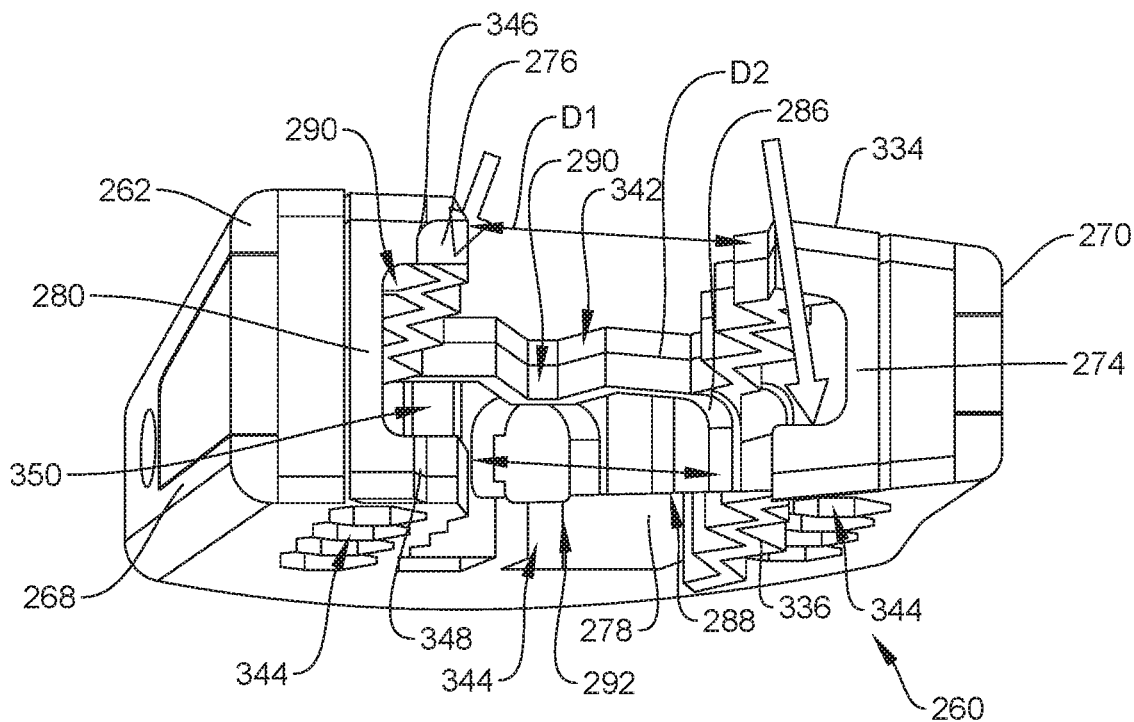
FIG. 38 is a perspective, cross-sectional view of the second component shown in FIG. 36.

Wall 276 and cap 334 define a ledge 346 that extends from ribs 280 of scaffold 274 to openings 286, 338 and wall 279 and cap 336 define a ledge 348 that extends from ribs 280 to openings 288, 340. Ledge 346 extends circumferentially about openings 286, 338 such that ledge 246 surrounds openings 286, 338. Likewise, ledge 348 extends circumferentially about openings 288, 340 such that ledge 246 surrounds openings 288, 340. Implant 260 includes a cavity 350 defined by inner surfaces of ribs 280. Openings 286, 288, 338, 340 each have a maximum diameter D1 that is less than a maximum diameter D2 of cavity 350, as shown in FIG. 38. Cavity 350 defines a graft containment area. In particular, it is envisioned that a material, such as, for example, bone graft BG can be inserted through openings 286, 338 and into cavity 350 or through openings 388, 340 and into cavity 350 to position bone graft BG between ledge 346 and ledge 348, as shown in FIG. 36.

In one embodiment, shown in FIGS. 42-47, system 100 includes an implant 352 that is similar to implant 260. Wall 264 of implant 352 includes a recessed portion 354 configured for disposal of at least a portion of engagement portion 136 of instrument 104. Implant 352 further includes a threaded bore 356 positioned between wall 268 of implant 352 and cavity 298 of implant 352 and a threaded bore 358 positioned between wall 270 of implant 352 and cavity 300 of implant 352. Bores 356, 358 are each configured for disposal of a fastener, such as, for example, a bone screw. Bores 356, 358 each extend at an oblique angle relative to axis X3 such that bores 356, 358 each extend through ledges 346, 348 of implant 352. In some embodiments, bore 356 includes an opening 356a that extends through cap 334 of implant 352 and an opening 356b that extends through cap 336 of implant 352 and wall 264 of implant 352. Bore 356 is free of any gaps or openings such that bore 356 is not in communication with cavity 350 of implant 352. In some embodiments, bore 358 includes an opening 358a that extends through cap 334 of implant 352 and an opening 358b that extends through cap 336 of implant 352 and wall 264 of implant 352. Bore 358 is free of any gaps or openings such that bore 358 is not in communication with cavity 350 of implant 352. In some embodiments, walls 264, 266 of implant 352 each have a maximum length that is greater than maximum lengths of walls 268, 270 of implant 352. In some embodiments, implant 352 is rounded at an interface between wall 264 of implant 352 and wall 268 of implant 352, at an interface between wall 268 of implant 352 and wall 266 of implant 352, at an interface between wall 266 of implant 352 and wall 270 of implant 352 and at an interface between wall 270 of implant 352 and wall 264 of implant 352.

Figure 49:
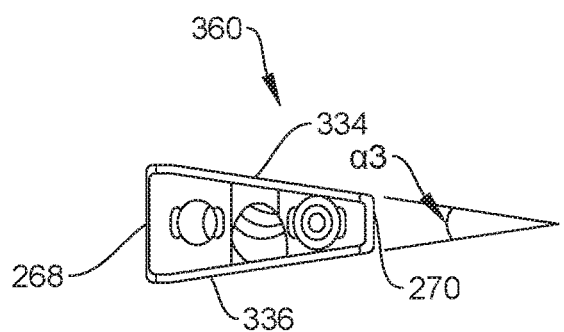
FIG. 49 is a front view of the second component shown in FIG. 48.
Figure 50:
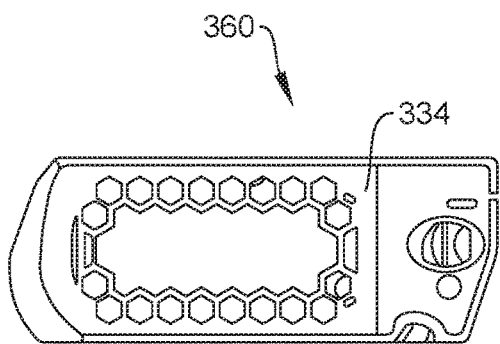
FIG. 50 is a top view of the second component shown in FIG. 48.
Figure 51:
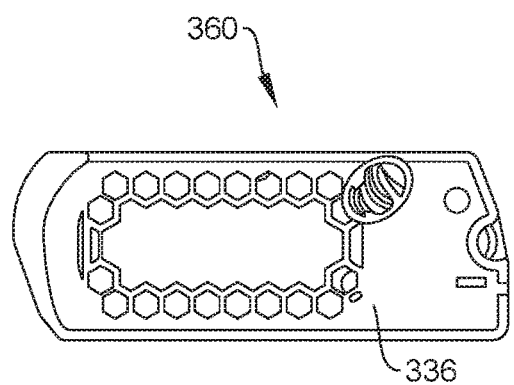
FIG. 51 is a bottom view of the second component shown in FIG. 48.
Figure 52:
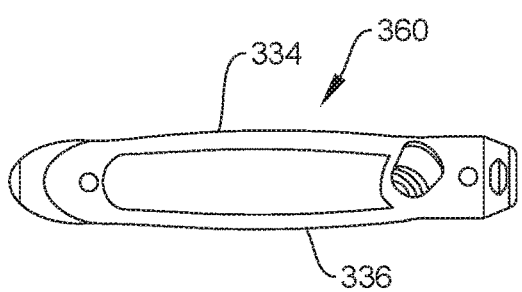
FIG. 52 is a side view of the second component shown in FIG. 48.
Figure 53:
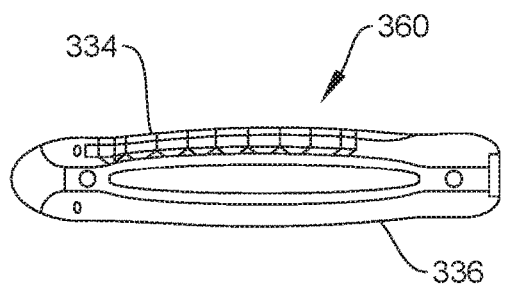
FIG. 53 is a rear view of the second component shown in FIG. 48.
Figure 54:
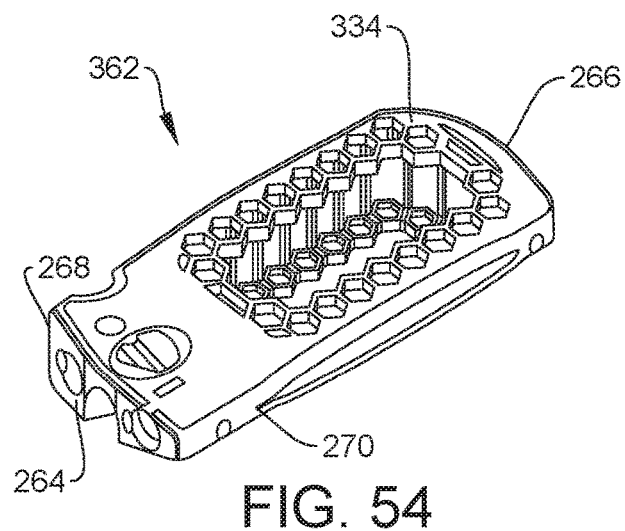
FIG. 54 is a perspective view of one embodiment of the second component of the spinal system shown in FIG. 1, in accordance with the principles of the present disclosure.

In one embodiment, shown in FIGS. 48-53, system 100 includes an implant 360 that is similar to implants 260, 352. Wall 268 of implant 360 has a height that is greater than a height of side wall 270 of implant 360 such that cap 334 of implant 360 is positioned at an angle α3 relative to cap 336 of implant 360, as shown in FIG. 49. Angle α3 provides implant 360 with a wedge-like shape. In some embodiments, angle α3 is between 0 degrees and 90 degrees. In some embodiments, angle α3 is between 1 degree and 89 degrees. In some embodiments, angle α3 is between 1 degree and 45 degrees. In some embodiments, angle α3 is between 10 degrees and 45 degrees. In some embodiments, angle α3 is between 10 degrees and 30 degrees. In some embodiments, angle α3 is between 15 degrees and 25 degrees. However, it is envisioned that angle α3 can be selected to be any angle that achieves proper lordosis when implant 360 is positioned between adjacent vertebrae. In some embodiments, walls 264, 266 of implant 360 each have a maximum length that is less than maximum lengths of walls 268, 270 of implant 360. In some embodiments, wall 264 of implant 360 extends at an acute angle relative to wall 268 of implant 360, wall 268 of implant 360 extends at an acute angle relative to wall 266 of implant 360, wall 266 of implant 360 extends at an acute angle relative to wall 270 of implant 360 and wall 270 of implant 360 extends at an acute angle relative to wall 264 of implant 360.

Figure 55:
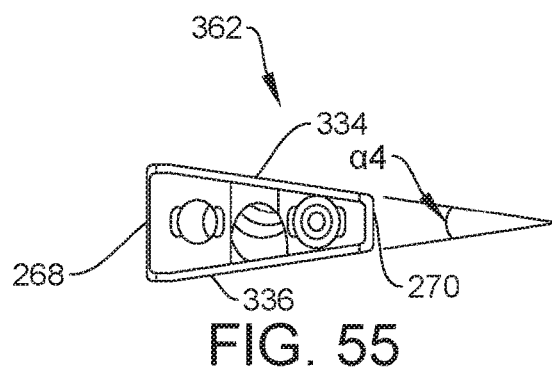
FIG. 55 is a front view of the second component shown in FIG. 54.
Figure 56:
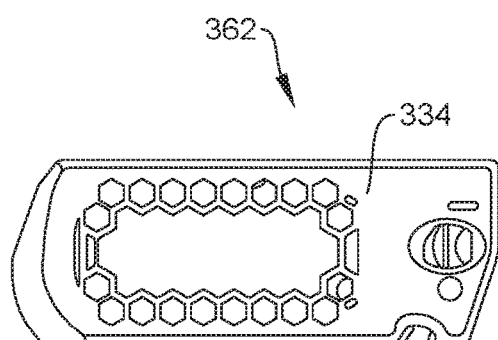
FIG. 56 is a top view of the second component shown in FIG. 54.
Figure 57:
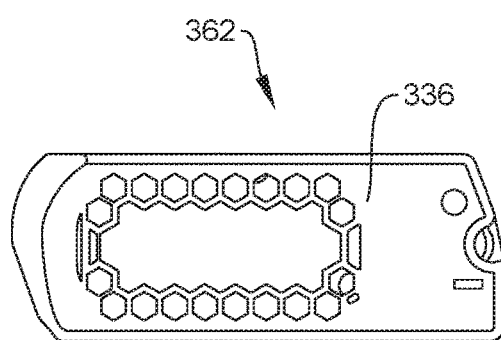
FIG. 57 is a bottom view of the second component shown in FIG. 54.
Figure 58:
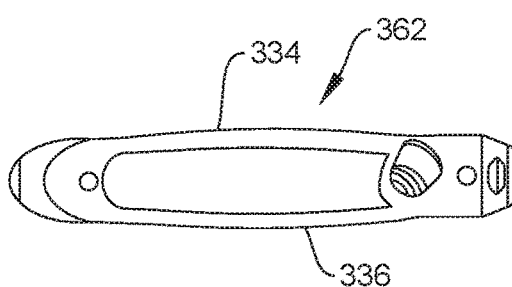
FIG. 58 is a side view of the second component shown in FIG. 54.
Figure 59:
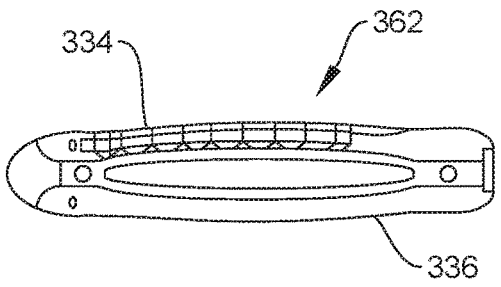
FIG. 59 is a rear view of the second component shown in FIG. 54.
Figure 60:
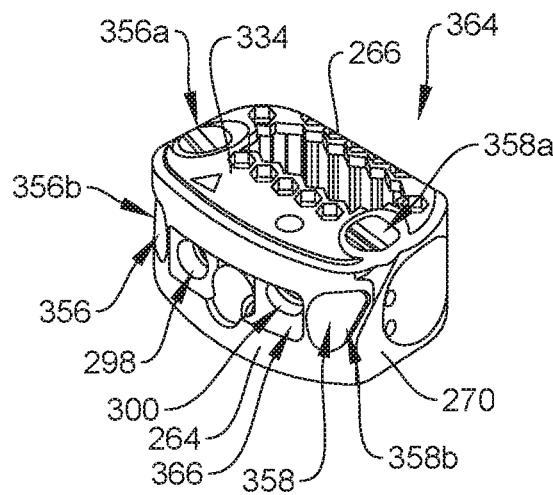
FIG. 60 is a perspective view of one embodiment of the second component of the spinal system shown in FIG. 1, in accordance with the principles of the present disclosure.
Figure 61:
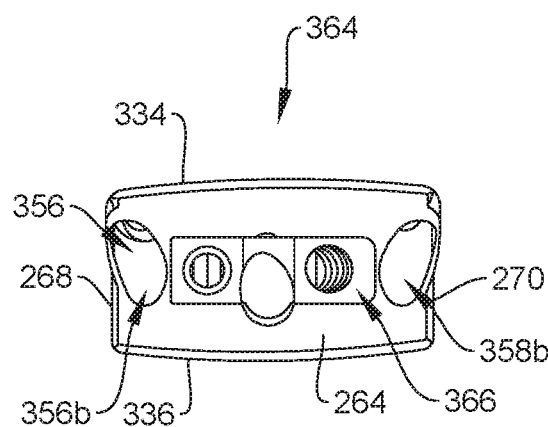
FIG. 61 is a front view of the second component shown in FIG. 60.
Figure 62:
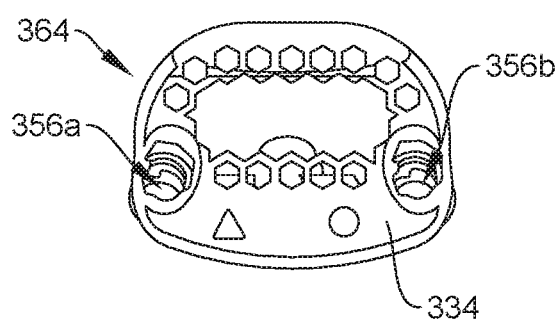
FIG. 62 is a top view of the second component shown in FIG. 60.

In one embodiment, shown in FIGS. 54-59, system 100 includes an implant 362 that is similar to implants 260, 352, 360. Wall 268 of implant 362 has a height that is greater than a height of side wall 270 of implant 362 such that cap 334 of implant 362 is positioned at an angle α4 relative to cap 336 of implant 362, as shown in FIG. 55. Angle α4 is less than angle α3. In some embodiments, angle α4 is between 0 degrees and 15 degrees. In some embodiments, angle α4 is between 1 degree and 15 degrees. In some embodiments, angle α4 is between 1 degree and 10 degrees. In some embodiments, angle α4 is between 1 degree and 5 degrees. However, it is envisioned that angle α4 can be selected to be any angle that achieves proper lordosis when implant 362 is positioned between adjacent vertebrae. In some embodiments, walls 264, 266 of implant 362 each have a maximum length that is less than maximum lengths of walls 268, 270 of implant 362. In some embodiments, wall 264 of implant 362 extends at an acute angle relative to wall 268 of implant 362, wall 268 of implant 362 extends at an acute angle relative to wall 266 of implant 362, wall 266 of implant 362 extends at an acute angle relative to wall 270 of implant 362 and wall 270 of implant 362 extends at an acute angle relative to wall 264 of implant 362.

Figure 63:
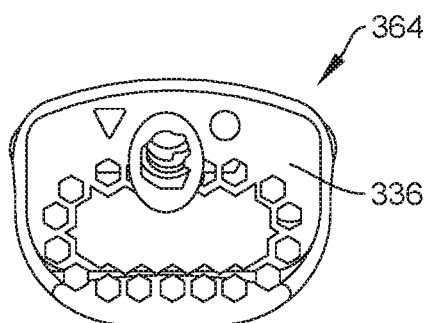
FIG. 63 is a bottom view of the second component shown in FIG. 60.
Figure 64:
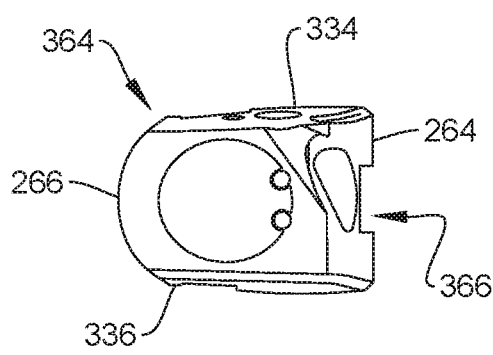
FIG. 64 is a side view of the second component shown in FIG. 60.
Figure 65:
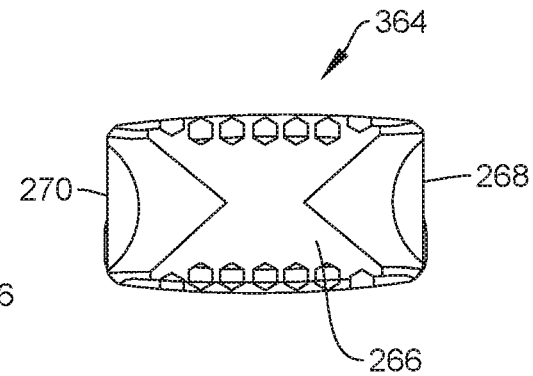
FIG. 65 is a rear view of the second component shown in FIG. 60.

In one embodiment, shown in FIGS. 60-65, system 100 includes an implant 364 that is similar to implants 260, 352, 360, 362. Wall 264 of implant 364 includes a recessed portion 366 configured for disposal of at least a portion of engagement portion 136 of instrument 104. Implant 364 further includes a threaded bore 356 positioned between wall 268 of implant 364 and cavity 298 of implant 364 and a threaded bore 358 positioned between wall 270 of implant 364 and cavity 300 of implant 364. Bores 356, 358 are each configured for disposal of a fastener, such as, for example, a bone screw. Bores 356, 358 each extend at an oblique angle relative to axis X3 such that bores 356, 358 each extend through ledges 346, 348 of implant 364. In some embodiments, bore 356 includes an opening 356a that extends through cap 334 of implant 364 and an opening 356b that extends through wall 264 of implant 364. Bore 356 is free of any gaps or openings such that bore 356 is not in communication with cavity 350. In some embodiments, bore 358 includes an opening 358a that extends through cap 334 of implant 364 and an opening 358b that extends through wall 264 of implant 364. Bore 358 is free of any gaps or openings such that bore 358 is not in communication with cavity 350. In some embodiments, neither bore 356 nor bore 358 extend through cap 336 of implant 364, as shown in FIG. 63. In some embodiments, walls 264, 266 of implant 364 each have a maximum length that is greater than maximum lengths of walls 268, 270 of implant 364. In some embodiments, implant 364 is rounded at an interface between wall 264 of implant 364 and wall 268 of implant 364, at an interface between wall 268 of implant 364 and wall 266 of implant 364, at an interface between wall 266 of implant 364 and wall 270 of implant 364 and at an interface between wall 270 of implant 364 and wall 264 of implant 364. In some embodiments, walls 264, 266, 268, 270 of implant 364 each have a height from cap 334 of implant 364 to cap 336 of implant 364 that is greater than heights of walls 264, 266, 268, 270 of implant 352 from cap 334 of implant 352 to cap 336 of implant 352.

In one embodiment, shown in FIGS. 66-71, system 100 includes an implant 368 that is similar to implants 260, 352, 360, 362, 364. Wall 268 of implant 368 has a height that is greater than a height of side wall 270 of implant 368 such that cap 334 of implant 368 is positioned at an angle α5 relative to cap 336 of implant 368, as shown in FIG. 67. Angle α5 provides implant 368 with a wedge-like shape. In some embodiments, angle α5 is between 0 degrees and 90 degrees. In some embodiments, angle α5 is between 1 degree and 89 degrees. In some embodiments, angle α5 is between 1 degree and 45 degrees. In some embodiments, angle α5 is between 10 degrees and 45 degrees. In some embodiments, angle α5 is between 10 degrees and 30 degrees. In some embodiments, angle α5 is between 15 degrees and 25 degrees. However, it is envisioned that angle α5 can be selected to be any angle that achieves proper lordosis when implant 368 is positioned between adjacent vertebrae. In some embodiments, walls 264, 266 of implant 368 each have a maximum length that is less than maximum lengths of walls 268, 270 of implant 368. In some embodiments, wall 264 of implant 368 extends at an acute angle relative to wall 268 of implant 368, wall 268 of implant 368 extends at an acute angle relative to wall 266 of implant 368, wall 266 of implant 368 extends at an acute angle relative to wall 270 of implant 368 and wall 270 of implant 368 extends at an acute angle relative to wall 264 of implant 368. In some embodiments, wall 264 of implant 368 includes a planar portion 264a, a planar portion 264b and a planar portion 264c positioned between planar portion 264a and planar portion 264b. Planar portion 264b extends at an acute angle relative to planar portion 264a and planar portion 264c extends at an acute angle relative to planar portion 264b. In some embodiments, planar portions 264a, 264b, 264c are configured for engagement with planar portions 138a, 138b, 138c of instrument 104 shown in FIG. 13.

In one embodiment, shown in FIGS. 72-77, system 100 includes an implant 370 that is similar to implants 260, 352, 360, 362, 364, 368. Side wall 268 of implant 370 has a height that is greater than a height of side wall 270 of implant 370 such that cap 334 of implant 370 is positioned at an angle α6 relative to cap 336 of implant 370, as shown in FIG. 73. Angle α6 provides implant 370 with a wedge-like shape. Angle α6 is less than angle α5. In some embodiments, angle α6 is between 0 degrees and 15 degrees. In some embodiments, angle α6 is between 1 degree and 15 degrees. In some embodiments, angle α6 is between 1 degree and 10 degrees. In some embodiments, angle α6 is between 1 degree and 5 degrees. However, it is envisioned that angle α6 can be selected to be any angle that achieves proper lordosis when implant 370 is positioned between adjacent vertebrae. In some embodiments, walls 264, 266 of implant 370 each have a maximum length that is less than maximum lengths of walls 268, 270 of implant 370. In some embodiments, wall 264 of implant 370 extends at an acute angle relative to wall 268 of implant 370, wall 268 of implant 370 extends at an acute angle relative to wall 266 of implant 370, wall 266 of implant 370 extends at an acute angle relative to wall 270 of implant 370 and wall 270 of implant 370 extends at an acute angle relative to wall 264 of implant 370. In some embodiments, wall 264 of implant 370 includes a planar portion 264a, a planar portion 264b and a planar portion 264c positioned between planar portion 264a and planar portion 264b. Planar portion 264b extends at an acute angle relative to planar portion 264a and planar portion 264c extends at an acute angle relative to planar portion 264b. In some embodiments, planar portions 264a, 264b, 264c are configured for engagement with planar portions 138a, 138b, 138c of instrument 104 shown in FIG. 13.

In one embodiment, shown in FIGS. 78-83, system 100 includes an implant 372 that is similar to implants 260, 352, 360, 362, 364, 368, 370. Wall 264 of implant 372 includes a recessed portion 354 configured for disposal of at least a portion of engagement portion 136 of instrument 104. Implant 372 further includes a threaded bore 356 positioned between wall 268 of implant 372 and cavity 298 of implant 372 and a threaded bore 358 positioned between wall 270 of implant 372 and cavity 300 of implant 372. Bores 356, 358 are each configured for disposal of a fastener, such as, for example, a bone screw. Bores 356, 358 each extend at an oblique angle relative to axis X3 such that bores 356, 358 each extend through ledges 346, 348 of implant 372. In some embodiments, bore 356 includes an opening 356a that extends through cap 334 of implant 372 and an opening 356b that extends through cap 336 of implant 372 and wall 264 of implant 372. Bore 356 is free of any gaps or openings such that bore 356 is not in communication with cavity 350 of implant 372. In some embodiments, bore 358 includes an opening 358a that extends through cap 334 of implant 372 and an opening 358b that extends through cap 336 of implant 372 and wall 264 of implant 372. Bore 358 is free of any gaps or openings such that bore 358 is not in communication with cavity 350 of implant 372. In some embodiments, walls 264, 266 of implant 372 each have a maximum length that is greater than maximum lengths of walls 268, 270 of implant 372. In some embodiments, implant 372 is rounded at an interface between wall 264 of implant 372 and wall 268 of implant 372, at an interface between wall 268 of implant 372 and wall 266 of implant 372, at an interface between wall 266 of implant 372 and wall 270 of implant 372 and at an interface between wall 270 of implant 372 and wall 264 of implant 372.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
an outer sleeve extending between opposite proximal and distal ends, the outer sleeve defining a passageway, the distal end defined by an engagement portion, the engagement portion extending from a first end to an opposite second end, the engagement portion comprising an aperture extending through a first end portion of the outer sleeve and an opening extending through a second end portion of the outer sleeve, the opening being in communication with the passageway;
an inner sleeve positioned in the passageway and comprising opposite proximal and distal ends, the distal end of the inner sleeve comprising a female thread; and
a knob coupled to the proximal end of the inner sleeve such that the knob is rotatable relative to the outer sleeve to rotate the inner sleeve relative to the outer sleeve, the inner sleeve being monolithically formed with the knob.

2. The surgical instrument recited in claim 1, wherein the aperture is spaced apart from the opening.

3. The surgical instrument recited in claim 1, wherein the aperture is not in communication with the passageway.

4. The surgical instrument recited in claim 1, wherein the inner sleeve is configured to translate within the passageway such that the distal end of the inner sleeve extends through the opening.

5. The surgical instrument recited in claim 1, wherein the second end is permanently fixed relative to the first end.

6. The surgical instrument recited in claim 1, wherein the aperture is non-threaded.

7. The surgical instrument recited in claim 1, wherein the aperture extends through a distalmost surface of the outer sleeve.

8. The surgical instrument recited in claim 1, wherein the opening extends through a distalmost surface of the outer sleeve.

9. The surgical instrument recited in claim 1, wherein the aperture and the opening each extend through a distalmost surface of the outer sleeve.

10. The surgical instrument recited in claim 1, wherein the knob is configured to translate axially relative to the outer sleeve to move the inner sleeve from a first orientation in which the female thread is disposed in the passageway to a second orientation in which the female thread is positioned outside of the passageway.

11. The surgical instrument recited in claim 1, wherein the inner sleeve is rotatably positioned within the passageway.

12. The surgical instrument recited in claim 1, wherein the inner sleeve comprises opposite inner and outer surfaces, the outer surface engaging an inner surface of the outer sleeve that defines the passageway, the inner surface defining the female thread.

13. The surgical instrument recited in claim 1, wherein the outer sleeve extends along a longitudinal axis between the proximal end of the outer sleeve and the distal end of the outer sleeve, the opening being extending along an axis that is coaxial with the longitudinal axis.

14. The surgical instrument recited in claim 1, wherein the outer sleeve extends along a longitudinal axis between the proximal end of the outer sleeve and the distal end of the outer sleeve, the aperture extending along an axis that is offset from the longitudinal axis.

15. The surgical instrument recited in claim 1, wherein the outer sleeve extends along a longitudinal axis between the proximal end of the outer sleeve and the distal end of the outer sleeve, the opening extending along an axis that is coaxial with the longitudinal axis, the aperture being offset from the longitudinal axis.

16. The surgical instrument recited in claim 1, wherein the inner sleeve is coupled directly to the knob such that the inner sleeve is fixed relative to the knob.

17. A surgical instrument comprising:
an outer sleeve extending along a longitudinal axis between opposite proximal and distal ends, the outer sleeve defining a passageway, the distal end defined by an engagement portion, the engagement portion extending from a first end to an opposite second end, the engagement portion comprising an aperture extending through a first end portion of the outer sleeve and an opening extending through a second end portion of the outer sleeve, the opening being in communication with the passageway, the opening extending along an axis that is coaxial with the longitudinal axis, the aperture extending at an acute angle relative to the longitudinal axis;

an inner sleeve positioned in the passageway and comprising opposite proximal and distal ends, the distal end of the inner sleeve comprising a female thread; and a knob coupled to the proximal end of the inner sleeve such that the knob is rotatable relative to the outer sleeve to rotate the inner sleeve relative to the outer sleeve, the inner sleeve being monolithically formed with the knob.

18. A surgical instrument comprising:

an outer sleeve extending between opposite proximal and distal ends, the outer sleeve defining a passageway, the distal end defining an engagement portion extending from a first end to an opposite second end, the engagement portion comprising an aperture extending through the first end and an opening extending through the second end, the opening being in communication with the passageway;

an inner sleeve positioned in the passageway and comprising opposite proximal and distal ends, the distal end of the inner sleeve comprising a female thread; and a knob coupled to the proximal end of the inner sleeve such that the knob is rotatable relative to the outer sleeve to rotate the inner sleeve relative to the outer sleeve, the inner sleeve being welded directly to the knob to couple the inner sleeve to the knob.

\* \* \* \* \*